United States Patent [19]

Rajopadhye et al.

[11] Patent Number: 5,888,970
[45] Date of Patent: Mar. 30, 1999

[54] TECHNETIUM-99M LABELED CHELATOR INCORPORATED CYCLIC PEPTIDES THAT BIND TO THE GPIIB/IIIA RECEPTOR AS IMAGING AGENTS

[75] Inventors: Milind Rajopadhye, Westford; Prahlad Ramadhar Singh, Arlington, both of Mass.

[73] Assignee: DuPont Pharmaceuticals Company, Wilmington, Del.

[21] Appl. No.: 940,825

[22] Filed: Oct. 1, 1997

Related U.S. Application Data

[60] Provisional application No. 60/027,359, Oct. 2, 1996.
[51] Int. Cl.$^6$ .......................... A61K 38/00; A61K 39/40; C07K 5/00; C07K 16/00
[52] U.S. Cl. ................................. 514/9; 514/11; 530/317; 424/1.69
[58] Field of Search ................................ 530/317; 514/9, 514/11

[56] References Cited

U.S. PATENT DOCUMENTS

| | | | |
|---|---|---|---|
| 5,443,816 | 8/1995 | Zamora et al. | 424/1.69 |
| 5,635,477 | 6/1997 | Degrado et al. | 514/11 |

OTHER PUBLICATIONS

Lister–James et al., Technetium and Rhenium in Chemistry and Nuclear Medicine SGEditoriali: Padova, 1995, 269–274, "Technetium–99m Chelate Containing Receptor–binding Peptides".

Lister–James et al., Journal of Nuclear Medicine 1995, 16P–17P, "Tc–99M P748. A Receptor–Binding Techtide™ for Imaging Activated Platelets".

Lister–James et al., Quarterly Journal of Nuclear Medicine 1996, 40, 221–233, "Small Peptides Radiolabeled with $^{99m}$Tc".

Knight et al., Journal of Nuclear Medicine 1994, 35, 282–288, "Thrombus Imaging with Technetium–99m Synthetic Peptides Based upon the Binding Domain of a Monoclonal Antibody to Activated Platelets".

Primary Examiner—Cecilia J. Tsang
Assistant Examiner—S. G. Marshall
Attorney, Agent, or Firm—David H. Vance

[57] ABSTRACT

The present invention describes novel radiopharmaceuticals of formula (I):

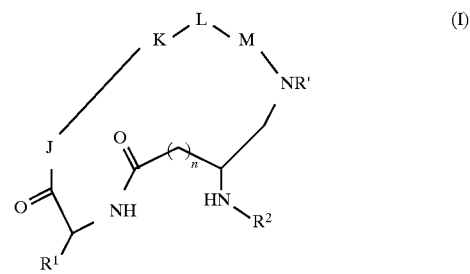

wherein J, K, L, and M, are amino acids or derivatives thereof and R', $R^1$, $R^2$ and n are as defined herein, that are radiolabeled cyclic compounds containing chelators which act as antagonists of the platelet glycoprotein IIb/IIIa complex, methods of using the same as imaging agents for the diagnosis of arterial and venous thrombi, and novel reagents for the preparation of the same and kits comprising the reagents.

19 Claims, No Drawings

TECHNETIUM-99M LABELED CHELATOR INCORPORATED CYCLIC PEPTIDES THAT BIND TO THE GPIIB/IIIA RECEPTOR AS IMAGING AGENTS

This application claims the benefit of U.S. Provisional Application Ser. No. 60/027359 filed on Oct. 2, 1996.

FIELD OF THE INVENTION

This invention relates to novel radiopharmaceuticals that are radiolabeled cyclic compounds containing chelators, methods of using the same as imaging agents for the diagnosis of arterial and venous thrombi, and novel reagents for the preparation of the same and kits comprising the reagents.

BACKGROUND OF THE INVENTION

The clinical recognition of venous and arterial thromboembolic disorders is unreliable, lacking in both sensitivity and specificity. In light of the potentially life threatening situation, the need to rapidly diagnose thromboembolic disorders using a non-invasive method is an unmet clinical need. Platelet activation and resulting aggregation has been shown to be associated with various pathophysiological conditions including cardiovascular and cerebrovascular thromboembolic disorders such as unstable angina, myocardial infarction, transient ischemic attack, stroke, atherosclerosis and diabetes. The contribution of platelets to these disease processes stems from their ability to form aggregates, or platelet thrombi, especially in the arterial wall following injury. See generally, Fuster et al., J. Am. Coll. Cardiol., Vol. 5, No. 6, pp. 175B–183B (1985); Rubenstein et al., Am. Heart J., Vol. 102, pp. 363–367 (1981); Hamm et al., J. Am. Coll. Cardiol., Vol. 10, pp. 998–1006 (1987); and Davies et al., Circulation, Vol. 73, pp. 418–427 (1986). Recently, the platelet glycoprotein IIb/IIIa complex (GPIIb/IIIa), has been identified as the membrane protein which mediates platelet aggregation by providing a common pathway for the known platelet agonists. See Philips et al., Cell, Vol. 65, pp. 359–362 (1991).

Platelet activation and aggregation is also thought to play a significant role in venous thromboembolic disorders such as venous thrombophlebitis and subsequent pulmonary emboli. It is also known that patients whose blood flows over artificial surfaces, such as prosthetic synthetic cardiac valves, are at risk for the development of platelet plugs, thrombi and emboli. See generally Fuster et al., J. Am. Coll. Cardiol., Vol. 5, No. 6, pp. 175B–183B (1985); Rubenstein et al., Am. Heart J., Vol. 102, pp. 363–367 (1981); Hamm et al., J. Am. Coll. Cardiol., Vol. 10, pp. 998–1006 (1987); and Davies et al., Circulation, Vol. 73, pp. 418–427 (1986).

A suitable means for the non-invasive diagnosis and monitoring of patients with such potential thromboembolic disorders would be highly useful, and several attempts have been made to develop radiolabeled agents targeted to platelets for non-invasive radionuclide imaging. For example, experimental studies have been carried out with 99mTc monoclonal antifibrin antibody for diagnostic imaging of arterial thrombus. See Cerqueira et al., Circulation, Vol., 85, pp. 298–304 (1992). The authors report the potential utility of such agents in the imaging of freshly formed arterial thrombus. Monoclonal antibodies labeled with 131I and specific for activated human platelets have also been reported to have potential application in the diagnosis of arterial and venous thrombi. However, a reasonable ratio of thrombus to blood (target/background) was only attainable at 4 hours after the administration of the radiolabeled antibody. See Wu et al., Clin. Med. J., Vol. 105, pp. 533–559 (1992). The use of 125I, 131I, 99mTc, and 111In radiolabeled 7E3 monoclonal antiplatelet antibody in imaging thrombi has also been recently discussed. Coller et al., PCT Application Publication No. WO 89/11538 (1989). The radiolabeled 7E3 antibody has the disadvantage, however, of being a very large molecular weight molecule. Other researchers have employed enzymatically inactivated t-PA radioiodinated with 123I, 125I and 131I for the detection and the localization of thrombi. See Ordm et al., Circulation, Vol. 85, pp. 288–297 (1992). Still other approaches in the radiologic detection of thromoboembolisms are described, for example, in Koblik et al., Semin. Nucl. Med., Vol. 19, pp. 221–237 (1989).

Arterial and venous thrombus detection and localization is of critical importance in accurately diagnosing thromboembolic disorders and determining proper therapy. New and better radiolabeled agents for non-invasive radionuclide imaging to detect thrombi are needed. The present invention is directed to this important end.

SUMMARY OF THE INVENTION

Accordingly, one object of the present invention is to provide novel reagents for making radiopharmaceuticals which act as antagonists of the platelet glycoprotein IIb/IIIa complex.

It is another object of the present invention is to provide novel radiopharmaceuticals which act as antagonists of the platelet glycoprotein IIb/IIIa complex.

It is another object of the present invention is to provide a method of using said radiopharmaceuticals as imaging agents for the diagnosis of arterial and venous thrombi.

It is another object of the present invention to provide novel radiopharmaceutical compositions for the diagnosis of arterial and venous thrombi.

It is another object of the present invention to provide novel kits comprising the reagents of the present invention for making radiopharmaceutical compositions.

These and other objects, which will become apparent during the following detailed description, have been achieved by the inventors' discovery that compounds of formula (I):

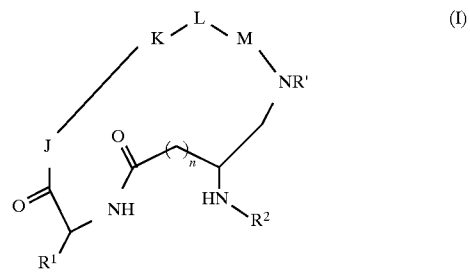

or a pharmaceutically acceptable salts or prodrugs thereof, wherein J, K, L, M, n, R', $R^1$ and $R^2$ are as define below, are effective reagents for making radiopharmaceuticals which act as antagonists of the platelet glycoprotein IIb/IIIa complex.

DETAILED DESCRIPTION OF PREFERRED EMBODIMENTS

[1] Thus, in a first embodiment, the present invention provides a novel reagent for preparing a radiopharmaceutical of formula (I):

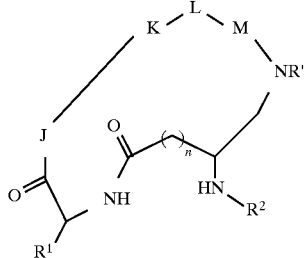

(I)

or a pharmaceutically acceptable salt or prodrug form thereof, wherein:

R' is H or $C_1$–$C_8$ alkyl;

$R^1$ is selected from the group:
H,
$C_1$–$C_4$ alkyl substituted with 0–3 $R^{20}$,
$C_{6-10}$ aryl substituted with 0–3 $R^{20a}$,
$C_{3-8}$ cycloalkyl substituted with 0–3 $R^{20a}$,
—$C_{6-10}$ aryl($C_{1-4}$ alkyl) substituted with 0–3 $R^{20a}$, and
a 5–10-membered heterocyclic ring system, containing 1–4 heteroatoms independently selected from N, S, and O, substituted with 0–1 $R^{20a}$;

$R^{20}$ is independently selected at each occurrence from the group:
$R^{20a}$;
$C_{6-10}$ aryl substituted with 0–1 $R^{20a}$; and,
a 5–10-membered heterocyclic ring system, containing 1–4 heteroatoms independently selected from N, S, and O, substituted with 0–1 $R^{20a}$;

$R^{20a}$ is independently selected at each occurrence from the group: —CN, —$CO_2R^{21}$, —C(=O)$R^{21a}$, C(=O)$CH_2OR^{21}$, C(=O)N$R^{22}$C(=O)$R^{21a}$, C(=O)$OCH_2CO_2H$, C(=O)N$R^{23}R^{24}$, —C(=O)N($R^{22}$)$_2$, —$CH_2OR^{21}$, —OC(=O)$R^{21a}$, —OC(=O)O$R^{21a}$, —O$R^{21a}$, —OC(=O)N($R^{22}$)$_2$, —N$R^{22}$C(=O)$R^{21a}$, —N$R^{22}$C(=O)O$R^{21}$, —N$R^{22}$C(=O)N($R^{22}$)$_2$, —N($R^{22}$)$_2$, =NO$R^{21}$, —C(=O)NHO$R^{21}$, —C(=O)NHN$R^{22}R^{22}$, —OCH$_2$CO$_2$H, N$R^{23}R^{24}$, —N$R^{22}$SO$_2$N($R^{22}$)$_2$, —N$R^{22}$SO$_2R^{21b}$, —SO$_3$H, —SO$_2R^{21b}$, —S$R^{21}$, —S(=O)$R^{21b}$, —SO$_2$N($R^{22}$)$_2$, SCH$_2$N$R^{22}$C(=O)$R^{21}$, SH, S(Pg), =O, OH, P$R^{25}R^{26}$, P(O)$R^{25}R^{26}$, P(S)$R^{25}R^{26}$, P(N$R^{27}$)$R^{25}R^{26}$; and a 5–10-membered heterocyclic ring system containing 1–4 heteroatoms independently selected from N, S, and O;

$R^{21}$ is independently selected at each occurrence from the group: H, $C_1$–$C_6$ alkyl, phenyl, benzyl, and trifluoromethyl;

$R^{21a}$ is independently selected at each occurrence from the group: H, $C_1$–$C_6$ alkyl, phenyl, benzyl, OH, $C_1$–$C_6$ alkoxy, halide, and trifluoromethyl;

$R^{21b}$ is independently selected at each occurrence from the group: $C_1$–$C_6$ alkyl, phenyl, benzyl, $C_1$–$C_6$ alkoxy, and trifluoromethyl;

$R^{22}$ is independently selected at each occurrence from the group: H, $C_1$–$C_6$ alkyl, phenyl, benzyl, cyano, and trifluoromethyl;

$R^{23}$, $R^{24}$, $R^{25}$, $R^{26}$, and $R^{27}$ are each independently selected at each occurrence from the group:
hydrogen;
$C_{1-10}$ alkyl substituted with 0–3 $R^{40}$;
$C_{6-10}$ aryl substituted with 0–3 $R^{40}$;
$C_{3-8}$ cycloalkyl substituted with 0–3 $R^{40}$;
heterocyclyl-$C_{1-6}$ alkyl substituted with 0–3 $R^{40}$, wherein the heterocycle is selected from the group: pyridine, pyrazine, proline, furan, thiofuran, thiazole, and diazine;
—$C_{6-10}$ aryl($C_{1-6}$ alkyl) substituted with 0–3 $R^{40}$;
—$C_{1-6}$ alkyl($C_{6-10}$ aryl) substituted with 0–3 $R^{40}$; and
an electron, provided that when one of $R^{23}$ or $R^{24}$ is an electron, then the other is also an electron, and provided that when one of $R^{25}$ or $R^{26}$ is an electron, then the other is also an electron;

$R^{40}$ is selected from the group: $C_{1-6}$ alkyl, phenyl, halo, —NO$_2$, —CN, —CO$_2R^{21}$, —C(=O)$R^{21a}$, C(=O)N($R^{22}$)$_2$, —CH$_2$O$R^{21}$, —OC(=O)$R^{21a}$, —O$R^{21a}$, —N$R^{22}$C(=O)$R^{21a}$, —N($R^{22}$)$_2$, —C(=O)NHO$R^{21}$, —C(=O)NHN$R^{22}R^{22}$, —N$R^{22}$SO$_2R^{21b}$, —SO$_3$H, —SO$_2R^{21b}$, —S$R^{21}$, —S(=O)$R^{21b}$, and —SO$_2$N($R^{22}$)$_2$;

$R^2$ is independently selected at each occurrence from the group:
H,
$C_1$–$C_4$ alkyl substituted with 0–3 $R^{41}$,
$C_{6-10}$ aryl substituted with 0–3 $R^{41a}$,
$C_{3-8}$ cycloalkyl substituted with 0–3 $R^{41a}$,
—$C_{6-10}$ aryl($C_{1-4}$ alkyl) substituted with 0–3 $R^{41a}$, and
a 5–10-membered heterocyclic ring system, containing 1–4 heteroatoms independently selected from N, S, and O, substituted with 0–1 $R^{20a}$;

$R^{41}$ is independently selected at each occurrence from the group:
$R^{41a}$;
$C_{6-10}$ aryl substituted with 0–1 $R^{41a}$; and,
a 5–10-membered heterocyclic ring system, containing 1–4 heteroatoms independently selected from N, S, and O, substituted with 0–1 $R^{41a}$;

$R^{41a}$ is independently selected at each occurrence from the group: N$R^{23}R^{24}$, =S, SH, S(Pg), =O, OH, P$R^{25}R^{26}$, P(O)$R^{25}R^{26}$, P(S)$R^{25}R^{26}$, and P(N$R^{27}$)$R^{25}R^{26}$;

provided that at least one of $R^1$ and $R^2$ contains at least one group selected from N$R^{23}R^{24}$, S, =S, SH, S(Pg), O, =O, OH, P$R^{25}R^{26}$, P(O)$R^{25}R^{26}$, P(S)$R^{25}R^{26}$, and P(N$R^{27}$)$R^{25}R^{26}$;

J is β-Ala or an L-isomer or D-isomer amino acid of the formula —N($R^3$)C($R^4$)($R^5$)C(=O)—;

$R^3$ is H or $C_1$–$C_8$ alkyl;

$R^4$ is H or $C_1$–$C_3$ alkyl;

$R^5$ is independently selected from the group: H, F, Cl, Br, I, —CF$_3$, —CN, —CO$_2R^{13}$, —C(=O)$R^{13}$, —C(=O)N($R^{13}$)$_2$, —CHO, —CH$_2$O$R^{13}$, —OC(=O)$R^{13}$, —OC(=O)O$R^{13a}$, —O$R^{13}$, —OC(=O)N($R^{13}$)$_2$, —N$R^{13}$C(=O)$R^{13}$, —N$R^{14}$C(=O)O$R^{13a}$, —N$R^{13}$C(=O)N($R^{13}$)$_2$, —N$R^{14}$SO$_2$N($R^{13}$)$_2$, —N$R^{14}$SO$_2R^{13a}$, —SO$_3$H, —SO$_2R^{13a}$, —S$R^{13}$, —S(=O)$R^{13a}$, —SO$_2$N($R^{13}$)$_2$, —N($R^{13}$)$_2$, —NHC(=NH)NH$R^{13}$, —C(=NH)NH$R^{13}$, =NO$R^{13}$, NO$_2$, —C(=O)NHO$R^{13}$, —C(=O)NHN$R^{13}R^{13a}$, =NO$R^{13}$, —B($R^{34}$)($R^{35}$), —OCH$_2$CO$_2$H, 2-(1-morpholino)ethoxy, —SC(=NH)NH$R^{13}$, N$_3$, —Si(CH$_3$)$_3$, ($C_1$–$C_5$ alkyl)NH$R^{16}$;

$C_1$–$C_8$ alkyl substituted with 0–2 $R^{11}$;
$C_2$–$C_8$ alkenyl substituted with 0–2 $R^{11}$;
$C_2$–$C_8$ alkynyl substituted with 0–2 $R^{11}$;
$C_3$–$C_{10}$ cycloalkyl substituted with 0–2 $R^{11}$;
aryl substituted with 0–2 $R^{12}$;
a 5–10-membered heterocyclic ring system containing 1–4 heteroatoms independently selected from N, S, or O, said heterocyclic ring being substituted with 0–2 $R^{12}$;
—$C_0$–$C_6$ alkyl-X;
—(CH$_2$)$_{q'}$-phenyl-(CH$_2$)$_{q'}$—X, wherein substitution on the phenyl is 1,4;

—$CH_2$-cyclohexyl-$CH_2$X, wherein substitution on the cyclohexyl is 1,4; and,

—$(CH_2)_mS(O)_p(CH_2)_2X$;

$R^3$ and $R^4$ may also be taken together to form —$CH_2((CH_2)_nNHC(=NR^{13})N(R^{13})_2)CH_2$—

$R^3$ and $R^5$ can alternatively be taken together to form —$(CH_2)_t$— or —$CH_2S(O)_pC(CH_3)_2$—;

$R^4$ and $R^5$ can alternatively be taken together to form —$(CH_2)_u$—;

K is a D-isomer or L-isomer amino acid of the formula —$N(R^6)CH(R^7)C(=O)$—;

$R^6$ is H or $C_1$–$C_8$ alkyl;

$R^7$ is selected from the group:
—$C_1$–$C_7$ alkyl-X;
—$(CH_2)_{q'}$-phenyl-$(CH_2)_{q'}$—X, wherein substitution on the phenyl is 1,3 or 1,4;
—$(CH_2)_{q'}$-cyclohexyl-$(CH_2)_{q'}$—X, wherein substitution on the cyclohexyl is 1,3 or 1,4;

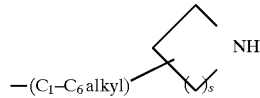

—$(CH_2)_mO$—$(C_1$–$C_4$ alkyl)-X; and,
—$(CH_2)_mS(O)_p$—$(C_1$–$C_4$ alkyl)-X;

X is selected from the group: $NHC(=NR^{13})N(R^{13})R^{13}$, —$N(R^{13})R^{13}$, —$C(=NH)(NH_2)$, —$SC(=NH)$—$NH_2$, —$NH$—$C(=NH)(NHCN)$, —$NH$—$C(=NCN)(NH_2)$, and —$NH$—$C(=N$—$OR^{13})(NH_2)$;

$R^6$ and $R^7$ can alternatively be taken together to form

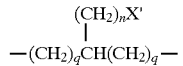

X' is —$NH_2$ or $NHC(=NR^{13})N(R^{13})R^{13}$;

L is —$Y(CH_2)_vC(=O)$—;

Y is NH, $N(C_1$–$C_3$ alkyl), O, or S;

M is a D-isomer or L-isomer amino acid of the formula

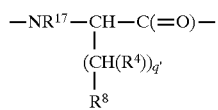

$R^{17}$ is H or $C_1$–$C_3$ alkyl;

$R^8$ is selected from the group: —$CO_2R^{13}$, —$SO_3R^{13}$, —$SO_2NHR^{14}$, —$B(R^{34})(R^{35})$, —$NHSO_2CF_3$, —$CONHNSO_2CF_3$, —$PO(OR^{13})_2$, —$PO(OR^{13})R^{13}$, —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$, and —$SO_2NH$-heteroaryl, said heteroaryl being 5–10-membered and having 1–4 heteroatoms selected independently from N, S, or O;

$R^{11}$ is independently selected at each occurrence from the group: =O, F, Cl, Br, I, —$CF_3$, —CN, —$CO_2R^{13}$, —$C(=O)R^{13}$, —$C(=O)N(R^{13})_2$, —CHO, —$CH_2OR^{13}$, —$OC(=O)R^{13}$, —$OC(=O)OR^{13a}$, —$OR^{13}$, —$OC(=O)N(R^{13})_2$, —$NR^{13}C(=O)R^{13}$, —$NR^{14}C(=O)OR^{13a}$, —$NR^{13}C(=O)N(R^{13})_2$, —$NR^{14}SO_2N(R^{13})_2$, —$NR^{14}SO_2R^{13a}$, —$SO_3H$, —$SO_2R^{13a}$, —$SR^{13}$, —$S(=O)R^{13a}$, —$SO_2N(R^{13})_2$, —$N(R^{13})_2$, —$NHC(=NH)NHR^{13}$, —$C(=NH)$
$NHR^{13}$, =$NOR^{13}$, $NO_2$, —$C(=O)NHOR^{13}$, —$C(=O)NHNR^{13}R^{13a}$, —$OCH_2CO_2H$, 2-(1-morpholino)ethoxy, $C_{1-6}$ alkyl, $C_2$–$C_4$ alkenyl, $C_3$–$C_6$ cycloalkyl, $C_3$–$C_6$ cycloalkylmethyl, $C_2$–$C_6$ alkoxy-$C_{1-6}$ alkyl, $C_3$–$C_6$ cycloalkoxy, and $C_{1-4}$ alkyl, said $C_{1-4}$ alkyl being substituted with 1–5 groups selected independently from the group: —$NR^{13}R^{14}$, —$CF_3$, $NO_2$, —$SO_2R^{13a}$, —$S(=O)R^{13a}$, $C_{6-10}$ aryl substituted with 0–2 $R^{12}$, and a 5–10-membered heterocyclic ring system containing 1–4 heteroatoms independently selected from N, S, and O, said heterocyclic ring being substituted with 0–2 $R^{12}$;

$R^{12}$ is independently at each occurrence selected from the group: phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_{6-10}$ aryl-$C_{1-6}$ alkyl, $C_1$–$C_5$ alkoxy, —$CO_2R^{13}$, —$C(=O)NHOR^{13a}$, —$C(=O)NHN(R^{13})_2$, =$NOR^{13}$, —$B(R^{34})(R^{35})$, $C_3$–$C_6$ cycloalkoxy, —$OC(=O)R^{13}$, —$C(=O)R^{13}$, —$OC(=O)OR^{13a}$, —$OR^{13}$, —$(C_1$–$C_4$ alkyl)—$OR^{13}$, —$N(R^{13})_2$, —$OC(=O)N(R^{13})_2$, —$NR^{13}C(=O)R^{13}$, —$NR^{13}C(=O)OR^{13a}$, —$NR^{13}C(=O)N(R^{13})_2$, —$NR^{13}SO_2N(R^{13})_2$, —$NR^{13}SO_2R^{13a}$, —$SO_3H$, —$SO_2R^{13a}$, —$S(=O)R^{13a}$, —$SR^{13}$, —$SO_2N(R^{13})_2$, $C_2$–$C_6$ alkoxyalkyl, methylenedioxy, ethylenedioxy, $C_1$–$C_4$ haloalkyl, $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, and $C_{1-4}$ alkyl, said $C_{1-4}$ being substituted with 1–5 groups selected independently from the group: —$N(R^{13})_2$, —$CF_3$, $NO_2$, and —$S(=O)R^{13a}$;

$R^{13}$ and $R^{13a}$ are selected independently at each occurrence from the group: H, $C_1$–$C_{10}$ alkyl, $C_3$–$C_{10}$ cycloalkyl, —$C_{14}$ alkyl-$C_{3-6}$ cycloalkyl, $C_{6-10}$ aryl, —$C_{1-10}$ alkyl-$C_{6-10}$ aryl, and $C_{1-6}$ alkoxy-$C_{1-6}$ alkyl;

when two $R^{13}$ groups are bonded to a single N, said $R^{13}$ groups may alternatively be taken together to form —$(CH_2)_{2-5}$— or —$(CH_2)O(CH_2)$—;

$R^{14}$ is selected from the group: OH, H, $C_1$–$C_4$ alkyl, and benzyl;

$R^{16}$ is selected from the group: an amine protecting group, 1–2 amino acids and 1–2 amino acids substituted with an amine protecting group;

$R^{34}$ and $R^{35}$ are independently at each occurrence selected from the group: —OH, —F, —$N(R^{13})_2$, and $C_1$–$C_8$-alkoxy;

$R^{34}$ and $R^{35}$ can alternatively be taken together form:
a cyclic boron ester where said chain or ring contains from 2 to 20 carbon atoms and, optionally, 1–4 heteroatoms independently selected from N, S, or O;
a divalent cyclic boron amide where said chain or ring contains from 2 to 20 carbon atoms and, optionally, 1–4 heteroatoms independently selected from N, S, or O; or
a cyclic boron amide-ester where said chain or ring contains from 2 to 20 carbon atoms and, optionally, 1–4 heteroatoms independently selected from N, S, or O;

Pg is a thiol protecting group;

m is 1 or 2;

n is 0, 1, or 2;

p' is 0, 1, or 2;

q is 1 or 2;

q' is 0, 1, or 2;

s is 0, 1, 2, or 3;
t is 2, 3, or 4;
u is 2, 3, 4, or 5; and,
v is 1 or 2.

[2] In a preferred embodiment, the present invention provides a reagent of formula (II):

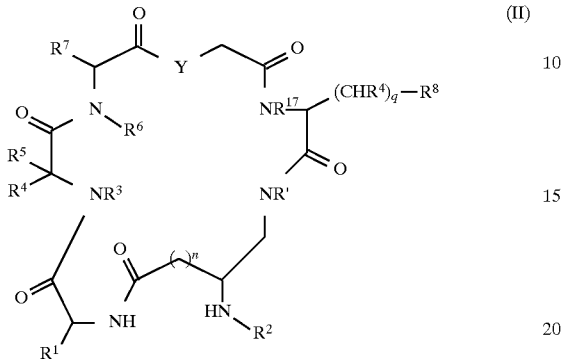

or a pharmaceutically acceptable salt or prodrug form thereof.

[3] In a more preferred embodiment, the present invention provides a reagent of formula (II), wherein R', $R^3$, $R^4$, $R^6$, and $R^{17}$ are independently selected from the group: H, methyl, and ethyl;

Y is NH;

$R^5$ is selected from the group:
  H, F, Cl, —$CF_3$, —CN, —$CO_2R^{13}$, —C(=O)$R^{13}$, —C(=O)N($R^{13}$)$_2$, —$CH_2OR^{13}$, —N($R^{13}$)$_2$,
  $C_1$–$C_8$ alkyl substituted with 0–2 $R^{11}$;
  $C_2$–$C_8$ alkenyl substituted with 0–2 $R^{11}$;
  $C_3$–$C_{10}$ cycloalkyl substituted with 0–2 $R^{11}$; aryl substituted with 0–2 $R^{12}$;
  a 5–10-membered heterocyclic ring system containing 1–4 heteroatoms independently selected from N, S, or O, said heterocyclic ring being substituted with 0–2 $R^{12}$;
  —$C_0$–$C_6$ alkyl-X;
  —(CH$_2$)$_{q'}$-phenyl-(CH$_2$)$_{q'}$—X, wherein substitution on the phenyl is 1,4;
  —CH$_2$-cyclohexyl-CH$_2$X, wherein substitution on the cyclohexyl is 1,4; and,
  —(CH$_2$)$_m$S(O)$_p$(CH$_2$)$_2$X;

$R^8$ is selected from the group: —$CO_2R^{13}$, —$SO_3R^{13}$, —$SO_2NHR^{14}$,
  —NHSO$_2$CF$_3$, —CONHNHSO$_2$CF$_3$, —PO(OR$^{13}$)$_2$, —PO(OR$^{13}$)R$^{13}$,
  —SO$_2$NHCOR$^{13}$, —CONHSO$_2$R$^{13a}$, —CH$_2$CONHSO$_2$R$^{13a}$, —NHSO$_2$NHCOR$^{13a}$,
  —NHCONHSO$_2$R$^{13a}$, —SO$_2$NHCONHR$^{13}$, and —SO$_2$NH-heteroaryl, said heteroaryl being 5–10-membered and having 1–4 heteroatoms selected independently from N, S, or O; and, $R^{12}$ is independently selected at each occurrence from the group: phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_{6\text{-}10}$ aryl-$C_{1\text{-}6}$ alkyl, $C_1$–$C_5$ alkoxy, —$CO_2R^{13}$, —C(=O)NHOR$^{13a}$, —C(=O)NHN(R$^{13}$)$_2$, =NOR$^{13}$, $C_3$–$C_6$ cycloalkoxy, —OC(=O)R$^{13}$, —C(=O)R$^{13}$, —OC(=O)OR$^{13a}$, —OR$^{13}$, —(C$_1$–C$_4$ alkyl)—OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, and $C_{1\text{-}4}$ alkyl, said $C_{1\text{-}4}$ being substituted with 1–5 groups selected independently from the group: —N(R$^{13}$)$_2$, —CF$_3$, NO$_2$, and —S(=O)R$^{13a}$.

[4] In an even more preferred embodiment, the present invention provides a novel reagent of formula (II), wherein $R^5$ is selected from the group:
  H;
  $C_1$–$C_8$ alkyl substituted with 0–2 $R^{11}$;
  aryl substituted with 0–2 $R^{12}$; and,
  a 5–10-membered heterocyclic ring system containing 1–4 heteroatoms independently selected from N, S, or O, said heterocyclic ring being substituted with 0–2 $R^{12}$;

X is selected from the group: NHC(=NR$^{13}$)N(R$^{13}$)R$^{13}$, —N(R$^{13}$)R$^{13}$, —C(=NH)(NH$_2$), and —NH—C(=N—OR$^{13}$)(NH$_2$);

$R^8$ is selected from the group: —CO$_2$R$^{13}$, —SO$_3$R$^{13}$, and —SO$_2$NHR$^{14}$; and, $R^{12}$ is independently selected at each occurrence from the group: phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_{6\text{-}10}$ aryl-$C_{1\text{-}6}$ alkyl, $C_1$–$C_5$ alkoxy, —CO$_2$R$^{13}$, $C_3$–$C_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —OCH$_2$CO$_2$H, and $C_{1\text{-}4}$ alkyl, said $C_{1\text{-}4}$ alkyl being substituted with 1–5 groups selected independently from the group: —N(R$^{13}$)$_2$, —CF$_3$, NO$_2$, and —S(=O)R$^{13a}$.

[5] In a further preferred embodiment, the present invention provides a novel reagent of formula (III):

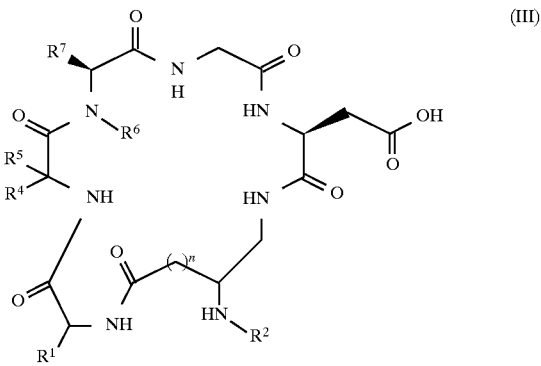

wherein, $R^1$ is $C_{1\text{-}4}$ alkyl substituted with 0–1 $R^{20a}$;

$R^{20a}$ is independently selected at each occurrence from the group: —CN, —CO$_2$R$^{21}$, —C(=O)R$^{21a}$, C(=O)CH$_2$OR$^{21}$, C(=O)NR$^{22}$C(=O)R$^{21a}$, C(=O)OCH$_2$CO$_2$H, C(=O)NR$^{23}$R$^{24}$, —C(=O)N(R$^{22}$)$_2$, —CH$_2$OR$^{21}$, —OC(=O)R$^{21a}$, —OC(=O)OR$^{21a}$, —OR$^{21a}$, —OC(=O)N(R$^{22}$)$_2$, —NR$^{22}$C(=O)R$^{21a}$, —NR$^{22}$C(=O)OR$^{21}$, —NR$^{22}$C(=O)N(R$^{22}$)$_2$, —N(R$^{22}$)$_2$, =NOR$^{21}$, —C(=O)NHOR$^{21}$, —C(=O)NHNR$^{22}$R$^{22}$, —OCH$_2$CO$_2$H, NR$^{23}$R$^{24}$, —NR$^{22}$SO$_2$N(R$^{22}$)$_2$, —NR$^{22}$SO$_2$R$^{21b}$, —SO$_3$H, —SO$_2$R$^{21b}$, —SR$^{21}$, —S(=O)R$^{21b}$, —SO$_2$N(R$^{22}$)$_2$, SCH$_2$NR$^{22}$C (=O)R$^{21}$, SH, S(Pg), =O, OH, PR$^{25}$R$^{26}$, P(O)R$^{25}$R$^{26}$, P(S)R$^{25}$R$^{26}$, and P(NR$^{27}$)R$^{25}$R$^{26}$;

R$^{23}$, R$^{24}$, R$^{25}$, R$^{26}$, and R$^{27}$ are each independently selected at each occurrence from the group:
hydrogen;
  $C_{1-10}$ alkyl substituted with 0–3 R$^{40}$;
  $C_{6-10}$ aryl substituted with 0–3 R$^{40}$;
  $C_{3-8}$ cycloalkyl substituted with 0–3 R$^{40}$;
  heterocyclyl-$C_{1-6}$ alkyl substituted with 0–3 R$^{40}$, wherein the heterocycle is selected from the group:
    pyridine, pyrazine, proline, furan, thiofuran, thiazole, and diazine; and
  an electron, provided that when one of R$^{23}$ or R$^{24}$ is an electron, then the other is also an electron, and provided that when one of R$^{25}$ or R$^{26}$ is an electron, then the other is also an electron;

R$^2$ is independently selected from the group: H, and $C_{1-4}$ alkyl substituted with 0–1 R$^{41}$;

R$^5$ is selected from the group:
  H;
  $C_{1-4}$ alkyl substituted with 0–2 R$^{11}$;
  aryl substituted with 0–2 R$^{12}$; and,
  a 5–10-membered heterocyclic ring system containing 1–4 heteroatoms independently selected from N, S, or O, said heterocyclic ring being substituted with 0–2 R$^{12}$;

R$^7$ is selected from the group:
  —$C_1$–$C_7$ alkyl-X; and,
  —(CH$_2$)$_{q}$-phenyl-(CH$_2$)q'—X, wherein substitution on the phenyl is 1,3 or 1,4;

X is selected from the group: NHC(=NR$^{13}$)N(R$^{13}$)R$^{13}$, —N(R$^{13}$)R$^{13}$, —C(=NH) (NH$_2$), and —NH—C(=N—OR$^{13}$) (NH$_2$);

R$^{11}$ is independently selected at each occurrence from the group: =O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OR$^{13}$, —NR$^{13}$C(=O)R$^{13}$, —NR$^{14}$SO$_2$R$^{13a}$, —N(R$^{13}$)$_2$, —NHC(=NH)NHR$^{13}$, —C(=NH)NHR$^{13}$, $C_3$–$C_6$ cycloalkyl, $C_3$–$C_6$ cycloalkoxy, $C_{6-10}$ aryl substituted with 0–2 R$^{12}$, and a 5–10-membered heterocyclic ring system containing 1–4 heteroatoms independently selected from N, S, and O, said heterocyclic ring being substituted with 0–2 R$^{12}$;

R$^{12}$ is independently selected at each occurrence from the group: halogen, hydroxy, nitro, cyano, $C_1$–$C_5$ alkyl, $C_1$–$C_5$ alkoxy, —C$_2$R$^{13}$, $C_3$–$C_6$ cycloalkoxy, —C(=O)R$^{13}$, —OR$^{13}$, —N(R$^{13}$)$_2$, methylenedioxy, ethylenedioxy, $C_1$–$C_4$ haloalkyl, and $C_1$–$C_4$ haloalkoxy; and, R$^{13}$ is independently selected at each occurrence from the group: H, $C_1$–$C_{10}$ alkyl, $C_3$–$C_{10}$ cycloalkyl, $C_{1-4}$ alkyl-$C_{3-6}$ cycloalkyl, $C_{6-10}$ aryl, —$C_{1-10}$ alkyl-$C_{6-10}$ aryl, and $C_{1-6}$ alkoxy-$C_{1-6}$ alkyl.

[6] In a still further preferred embodiment, the present invention provides a reagent of formula (III), wherein R$^1$ is CH$_2$S(Pg) and R$^2$ is selected from H, CH$_2$CH$_2$S(Pg), C(O)CH$_2$S(Pg), CH$_2$C(CH$_3$)$_2$S(Pg), C(O)C(CH$_3$)$_2$S(Pg), CH$_2$(1-hydroxyphen-2-yl), and C(O)CH$_2$NH$_2$.

[7] In a still further preferred embodiment, the present invention provides a reagent of formula (III), wherein the reagent is selected from the group:

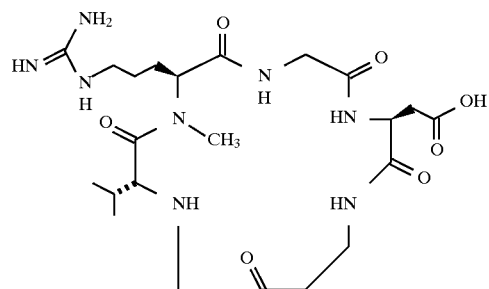

;

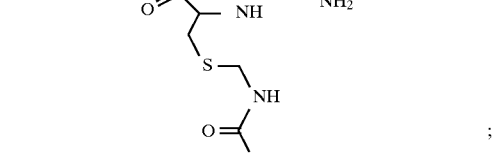

;

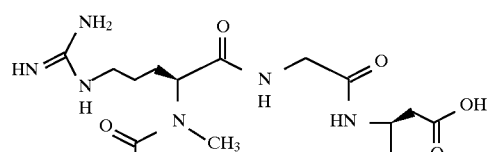

;

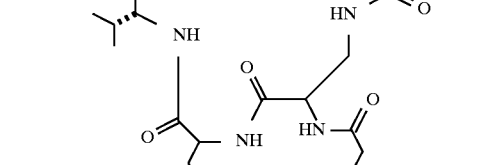

;

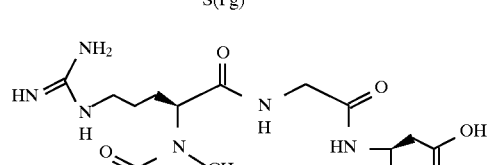

;

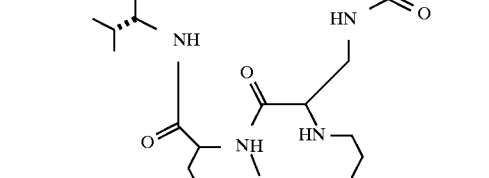

;

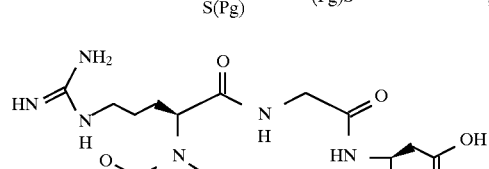

;

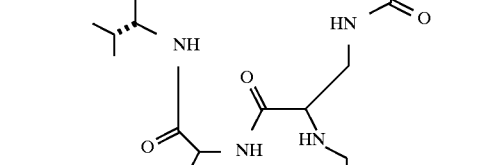

;

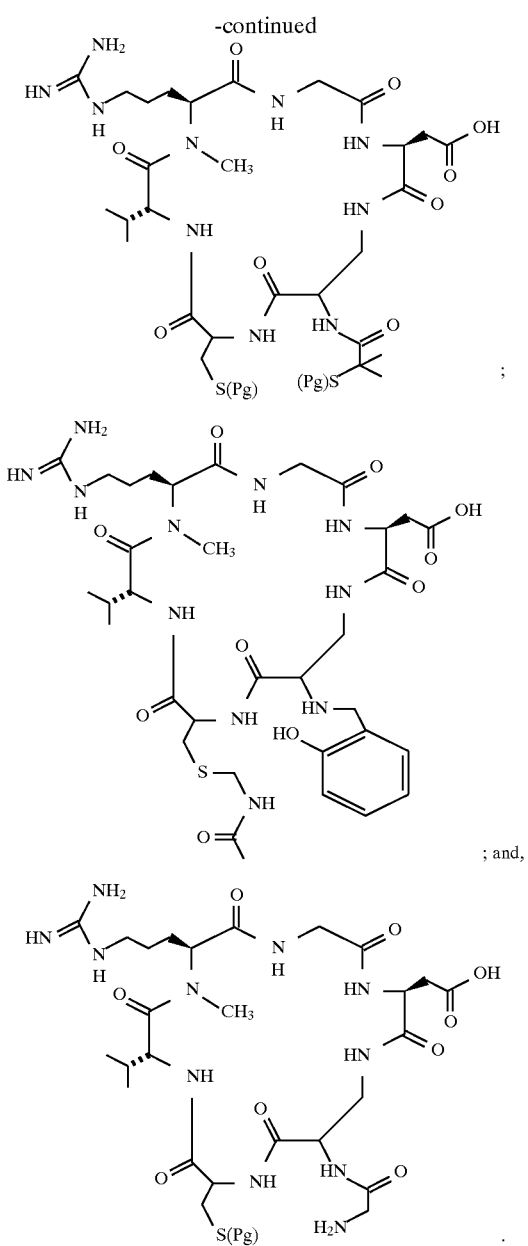

; and,

[8] In an even further preferred embodiment, Pg is selected from acetamidomethyl, 1-ethoxyethyl, p-anisylidene, tetrahydropyranyl, and tetrahydrofuranyl.

[9] In a second embodiment, the present invention provides a novel kit for preparing a radiopharmaceutical comprising a predetermined quantity of a sterile, pharmaceutically acceptable reagent of formula (I).

[10] In a third embodiment, the present invention provides a novel radiopharmaceutical comprising a complex of a reagent of formula (I) and a radionuclide selected from the group $^{99m}Tc$, $^{94m}Tc$, $^{95}Tc$, $^{111}In$, $^{62}Cu$, $^{43}Sc$, $^{45}Ti$, $^{67}Ga$, $^{68}Ga$, and $^{97}Ru$.

[11] In another more preferred embodiment, the present invention provides a radiopharmaceutical comprising a complex of a reagent of formula (I) and a radionuclide selected from the group $^{99m}Tc$, $^{111}In$, and $^{62}Cu$.

[12] In another even more preferred embodiment, the present invention provides a radiopharmaceutial of formula (I), wherein the radiopharmaceutical is selected from the group:

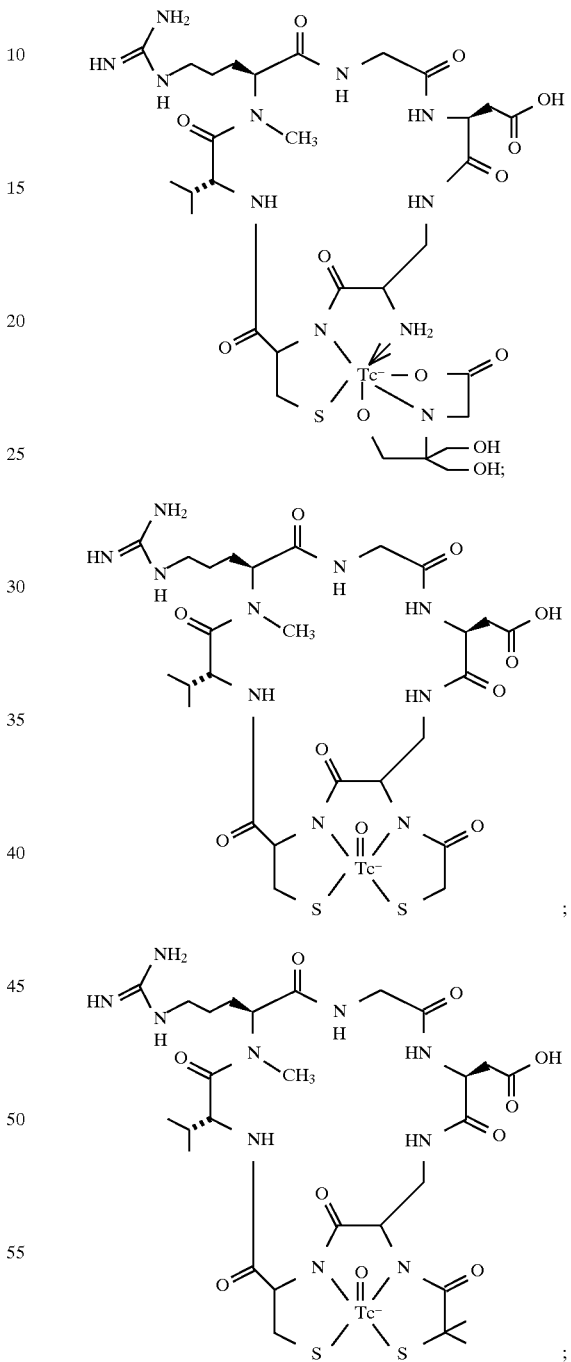

-continued

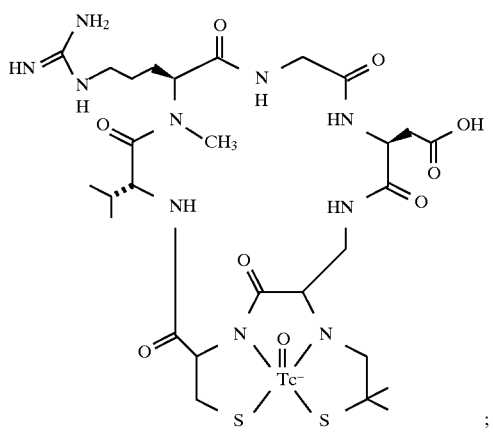

;

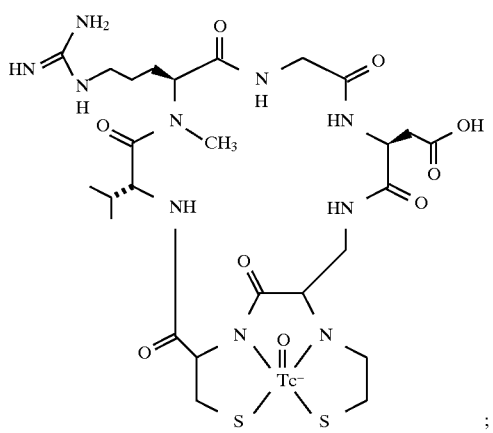

;

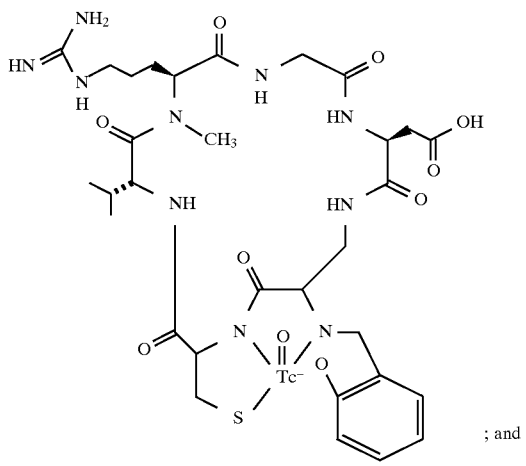

; and

-continued

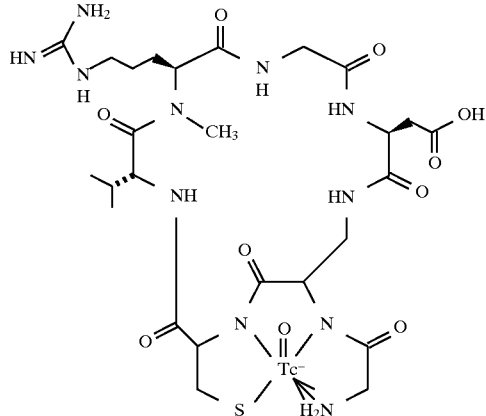

.

[13] In a fourth embodiment, the present invention provides a novel radiopharmaceutical composition comprising a radiopharmaceutically acceptable carrier and a radiolabeled compound of formula (I).

[14] In a fifth embodiment, the present invention provides a novel method for visualizing sites of platelet deposition in a mammal by radioimaging, comprising:

(i) administering to said mammal an effective amount of a radiopharmaceutical of formula (I), and (ii) scanning the mammal using a radioimaging devise.

[15] In a sixth embodiment, the present invention provides a novel method of determining platelet deposition in a mammal, comprising:

(a) administering to said mammal a radiopharmaceutical composition comprising a compound of formula (I), and (b) imaging said mammal.

[16] In a seventh embodiment, the present invention provides a novel method of diagnosing a disorder associated with platelet deposition in a mammal, comprising:

(a) administering to said mammal a radiopharmaceutical composition comprising a compound of formula (I), and (b) imaging said mammal.

[17] In an eighth embodiment, the present invention provides a novel sterile, non-pyrogenic kit for visualizing sites of platelet deposition, determining platelet deposition, or diagnosing a disorder associated with platelet deposition in a mammal, comprising:

(a) a predetermined quantity of a reagent of formula (I); and, (b) a predetermined quantity of a reducing agent.

[18] In another preferred embodiment, components (a) and (b) are contained in a vial.

[19] In another preferred embodiment, component (a) is contained in a first vial and component (b) is contained in a second vial.

As noted above, the cyclic compounds of the present invention may be radiolabeled. By "radiolabeled", it is meant that the subject cyclic platelet glycoprotein IIb/IIIa compounds contain a radioisotope which is suitable for administration to a mammalian patient. Suitable radioisotopes are known to those skilled in the art and include, for example, metals including technetium and indium. Preferred radioisotopes include $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, $^{97}$Ru, $^{72}$As, $^{82}$Rb, and $^{201}$Tl. Most preferred are $^{111}$In and $^{99m}$Tc. Radiolabeled compounds of the invention may be prepared using standard radiolabeling procedures well known to those skilled in the art. Suitable synthesis methodology is described in detail below.

The terms "metal chelator" and "chelator" are used interchangeably throughout to designate a chemical moiety capable of binding to or complexing with a metal nuclide.

As discussed below, the cyclic platelet glycoprotein IIb/IIIa compounds of the present invention may be radiolabeled by incorporating the radiolabel into the compounds through a chelating agent, where the chelating agent has been incorporated into the cyclic compounds. In formula (I), the metal chelator is intended to be the group:

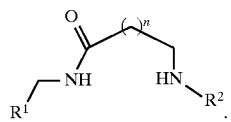

Also, the radiolabeling may be isotopic or nonisotopic. With isotopic radiolabeling, one group already present in the cyclic compounds described above is substituted with (exchanged for) the radioisotope. With nonisotopic radiolabeling, the radioisotope is added to the cyclic compounds without substituting with (exchanging for) an already existing group. All radiolabeled compounds, as well as isotopic and nonisotopic radiolabeled compounds are intended to be included within the phrase "radiolabeled compounds" as used in connection with the present invention. Such radiolabeling should also be reasonably stable, both chemically and metabolically, applying recognized standards in the art. Also, although the compounds of the invention may be labeled in a variety of fashions with a variety of different radioisotopes, as those skilled in the art will recognize, such radiolabeling should be carried out in a manner such that the high binding affinity and specificity of the unlabeled cyclic platelet GPIIb/IIIa compounds of the invention to the GPIIb/IIIa receptor is not significantly affected. By not significantly affected, it is meant that the binding affinity and specificity is not affected more than about 3 log units, preferably not more than about 2 log units, more preferably not more than about 1 log unit, even more preferably not more than about 500%, still even more preferably not more than about 250%, and most preferably the binding affinity and specificity is not affected at all.

For radiolabeled compounds, the label may appear at any position on compounds of the formula I, II, and III. Preferred radiolabeled compounds of the invention are radiolabeled compounds where the preferred metal nuclides, $^{99m}$Tc and $^{111}$In, are complexed at the chelator fragment involving $R^1$ and $R^2$.

It has been discovered that the radiolabeled compounds of the invention may be useful as radiopharmaceuticals for non-invasive imaging to diagnose present or potential thromboembolic disorders, such as arterial or venous thrombosis, including, for example, unstable angina, myocardial infarction, transient ischemic attack, stroke, atherosclerosis, diabetes, thrombophlebitis, pulmonary emboli, platelet plugs, and thrombi or emboli caused by prosthetic cardiac devices such as heart valves. The radiolabeled compounds of the invention may be useful with both newly formed and older thrombi. The radiolabeled compounds of the invention may also be used to diagnose other present or potential conditions where there is overexpression of the GPIIb/IIIa receptors, such as with metastatic cancer cells. The subject compounds may be effectively employed in low doses, thereby minimizing any risk of toxicity. Also, the subject compounds are of a much smaller size than, for example, the radiolabeled 7E3 antibodies known in the art, allowing easier attainment of suitable target/background (T/B) ratio for detecting thrombi. The use of the radiolabeled compounds of the invention is further described in the utility section below.

A "diagnostic kit," as used herein, comprises a collection of components, termed the formulation, in one or more vials which are used by the practising end user in a clinical or pharmacy setting to synthesize the radiopharmaceutical. The kit provides all the requisite components to synthesize and use the radiopharmaceutical except those that are commonly available to the practising end user, such as water or saline for injection, a solution of the radionuclide, equipment for heating the kit during the synthesis of the radiopharmaceutical if required, equipment necessary for administering the radiopharmaceutical to the patient such as syringes and shielding, and imaging equipment.

The present kits may be contained in one or more vials and all or part of the formulation can independently be in the form of a sterile solution or a lyophilized solid. It is preferred that reagent and reducing agent be lyophilized, when possible, to facilitate storage stability. If lyophilization is not practical, the kits can be stored frozen or in solution at room temperature. The solvents used are usually water or saline, preferably, water. Preferably, the kits are sealed.

The choice of radionuclides for diagnostic imaging will depend on the use and can be selected from radioactive isotopes Tc, Re, Ru, Co, Pt, Fe, Os, and Ir, preferably Tc or Re. Of course, because of availability of pertechnetate generators, such radionuclide is especially preferred. Due to the emission of both beta and gamma radiation, Re can be selected for both diagnostic and therapeutic purposes. Sterile non-pyrogenic containers (vials) which contain a predetermined quantity of sterile reagent of formula (I), and a predetermined quantity of a sterile reducing agent such as stannous chloride and which are capable of reducing a predetermined quantity of a preselected radionuclide are preferred.

A "buffer," as used herein, is a compound that is used to control the pH of the kit during its manufacture and during the synthesis of the radiopharmaceutical.

A "lyophilization aid," as used herein, is a component that has favorable physical properties for lyophilization, such as the glass transition temperature, and is added to the diagnostic kit to improve the physical properties of the combination of all the components of the kit for lyophilization.

A "stabilization aid," as used herein, is a component that is added to the radiopharmaceutical or to the diagnostic kit either to stabilize the radiopharmaceutical once it is synthesized or to prolong the shelf-life of the kit before it must be used. Stabilization aids can be antioxidants, reducing agents or radical scavengers and can provide improved stability by reacting preferentially with species that degrade other components or the radiopharmaceutical.

A "solubilization aid," as used herein, is a component that improves the solubility of one or more other components in the medium required for the synthesis of the radiopharmaceutical.

A "bacteriostat," as used herein, is a component that inhibits the growth of bacteria in the diagnostic kit either during its storage before use of after the kit is used to synthesize the radiopharmaceutical.

A "reducing agent," as used herein, is a compound that reacts with the radionuclide, which is typically obtained as a relatively unreactive, high oxidation state compound, to lower its oxidation state by transfering electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand," as used herein, is a ligand that forms an intermediate complex with the radionuclide that is stable enough to prevent unwanted side-reactions but labile enough to be converted to the radiopharmaceutical. The formation of the intermediate complex is kinetically favored while the formation of the radiopharmaceutical is thermodynamically favored. Transfer ligands useful in the preparation of radiopharmaceuticals and in diagnostic kits useful for the preparation of said radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present invention. Unless otherwise specifically noted, the L-isomer (or equivalent R or S configuration) of the amino acid is preferably used at all positions of the compounds of the present invention. Except as provided in the preceding sentence, all chiral, diastereomeric, racemic forms and all geometric isomeric forms of a structure are intended, unless the specific stereochemistry or isomer form is specifically indicated. The D and L-isomers of a particular amino acid are designated herein using the conventional 3-letter abbreviation of the amino acid, as indicated by the following examples: D-Leu, D-Leu, L-Leu, or L-Leu.

When any variable occurs more than one time in any constituent or in any formula, its definition on each occurrence is independent of its definition at every other occurrence. Thus, for example, if a group is shown to be substituted with 0–2 $R^{11}$, then said group may optionally be substituted with up to two $R^{11}$ and $R^{11}$ at each occurrence is selected independently from the defined list of possible $R^{11}$. Also, by way of example, for the group —N($R^{13}$)$_2$, each of the two $R^{13}$ substituents on N is independently selected from the defined list of possible $R^{13}$. When a bond to a substituent is shown to cross the bond connecting two atoms in a ring, then such substituent may be bonded to any atom on the ring. Combinations of substituents, variables, or both are permissible only if such combinations result in stable compounds.

Pg is selected from a variety of thiol protecting groups capable of being displaced upon reaction with a radionuclide, or deprotected under the reaction (radiolabeling) conditions. Such thiol protecting groups include those listed in Greene and Wuts, "Protective Groups in Organic Synthesis" John Wiley & Sons, New York (1991), the disclosure of which is hereby incorporated by reference. Any thiol protecting group known by those skilled in the art can be used. Examples of preferred thiol protecting groups include the following: acetamidomethyl (ACM), 1-ethoxyethyl (EOE), p-anisylidene, tetrahydropyranyl (THP), tetrahydrofuranyl (THF), and derivatives thereof.

By "stable compound" or "stable structure," it is intended herein to mean a compound that is sufficiently robust to survive isolation to a useful degree of purity from a reaction mixture and formulation into an efficacious therapeutic agent.

The term "substituted", as used herein, means that one or more hydrogens on the designated atom are replaced with a selection from the indicated group, provided that the designated atom's normal valency is not exceeded and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, including mono-,bi- or polycyclic ring systems, such as cyclopropyl, cyclobutyl, cyclopentyl, cyclohexyl, cycloheptyl, cyclooctyl and adamantyl; and "biycloalkyl" is intended to include saturated bicyclic ring groups such as [3.3.0]bicyclooctane, [4.3.0] bicyclononane, [4.4.0]bicyclodecane (decalin), [2.2.2] bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like. "Alkynyl" is intended to include hydrocarbon chains of either a straight or branched configuration and one or more triple carbon-carbon bonds which may occur in any stable point along the chain, such as ethynyl, propynyl and the like.

"Halo" or "halogen" as used herein refers to fluoro, chloro, bromo and iodo. "Counterion" is used to represent a small, negatively charged species such as chloride, bromide, hydroxide, acetate, sulfate and the like.

As used herein, "aryl" or "aromatic residue" is intended to mean an aromatic moiety containing the specified number of carbon atoms, such as phenyl or naphthyl. As used herein, "carbocycle" or "carbocyclic residue" is intended to mean any stable 3- to 7- membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic ring system" is intended to mean a stable 5- to 7- membered monocyclic or bicyclic or 7- to 10-membered bicyclic heterocyclic ring which may be saturated, partially unsaturated, or aromatic, and which consists of carbon atoms and from 1 to 4 heteroatoms selected independently from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, benzopyranyl, thiadiazine, tetrazolyl, benzofuranyl, benzothiophenyl, indolene, quinoline, isoquinolinyl or benzimidazolyl, piperidinyl, 4-piperidone, 2-pyrrolidone, tetrahydrofuran, tetrahydroquinoline, tetrahydroisoquinoline, decahydroquinoline, octahydroisoquinoline, azocine, triazine (including 1,2,3-, 1,2,4-, and 1,3,5-triazine), 6H-1,2,5-thiadiazine, 2H,6H-1,5, 2-dithiazine, thiophene, tetrahydrothiophene, thianthrene, furan, pyran, isobenzofuran, chromene, xanthene, phenoxathiin, 2H-pyrrole, pyrrole, imidazole, pyrazole, thiazole, isothiazole, oxazole (including 1,2,4- and 1,3,4-oxazole), isoxazole, triazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, β-carboline, phenanthridine, acridine, perimidine, phenanthroline, phenazine, phenarsazine, phenothiazine, furazan, phenoxazine, isochroman, chroman, pyrrolidine, pyrroline, imidazolidine, imidazoline, pyrazolidine, pyrazoline, piperazine, indoline, isoindoline, quinuclidine, or morpholine. Also included are fused ring and spiro compounds containing, for example, the above heterocycles.

As used herein, the term "any group that, when administered to a mammalian subject, cleaves to form a free hydroxyl, amino or sulfhydryl" means any group bonded to an O, N, or S atom, respectively, which is cleaved from the O, N, or S atom when the compound is administered to a mammalian subject to provide a compound having a remaining free hydroxyl, amino, or sulfhydryl group, respectively. Examples of groups that, when administered to a mammalian subject, are cleaved to form a free hydroxyl, amino or sulfhydryl, include but are not limited to, $C_1$–$C_6$ alkyl substituted with 0–3 $R^{11}$, $C_3$–$C_6$ alkoxyalkyl substituted with 0–3 $R^{11}$, $C_1$–$C_6$ alkylcarbonyl substituted with 0–3 $R^{11}$, $C_1$–$C_6$ alkoxycarbonyl substituted with 0–3 $R^{11}$, $C_1$–$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$. Examples of groups that, when administered to a mammalian subject, are cleaved to form a free hydroxyl, amino or sulfhydryl, include hydroxy, amine or sulfhydryl protecting groups, respectively.

As used herein, the term "amine protecting group" means any group known in the art of organic synthesis for the protection of amine groups. Such amine protecting groups include those listed in Greene and Wuts, "Protective Groups in Organic Synthesis" John Wiley & Sons, New York (1991) and "The Peptides: Analysis, Sythesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. Also included in the term "amine protecting group" are acyl groups such as azidobenzoyl, p-benzoylbenzoyl, o-benzylbenzoyl, p-acetylbenzoyl, dansyl, glycyl-p-benzoylbenzoyl, phenylbenzoyl, m-benzoylbenzoyl, benzoylbenzoyl.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The term "amino acid" as used herein means an organic compound containing both a basic amino group and an acidic carboxyl group. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, ornithine, 2,4-diaminobutyric acid, 2,3-diaminopropionic acid, beta-2-thienylalanine, 4-aminophenylalanine, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide. The term "peptide" as used herein means a linear compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

A "pseudopeptide" or "peptide mimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseudopeptide residue" means that portion of a pseudopeptide or peptide mimetic (as defined herein) that is present in a peptide.

The term "peptide bond" means a covalent amide linkage formed by loss of a molecule of water between the carboxyl group of one amino acid and the amino group of a second amino acid. The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The term "ring substituted cyclizing moiety" is a cyclizing moiety bearing a substituent group one or more of its carbocyclic or heterocyclic rings.

The term "cyclic compound intermediate" means the intermediate compound that serves as the precursor to the claimed compounds.

The phrase "boronic acid" as used herein means a group of the formula —B($R^{34}$)($R^{35}$), wherein $R^{34}$ and $R^{35}$ are independently selected from: —OH; —F; —$NR^{13}R^{14}$; or $C_1$–$C_8$-alkoxy; or $R^{34}$ and $R^{35}$ can alternatively be taken together to form: a cyclic boron ester where said chain or ring contains from 2 to 20 carbon atoms and, optionally, 1–4 heteroatoms independently selected from N, S, or O; a divalent cyclic boron amide where said chain or ring contains from 2 to 20 carbon atoms and, optionally, 1–4 heteroatoms independently selected from N, S, or O; a cyclic boron amide-ester where said chain or ring contains from 2 to 20 carbon atoms and, optionally, 1–4 heteroatoms independently selected from N, S, or O. Such cyclic boron esters, boron amides, or boron amide-esters may also be optionally substituted with 1–5 groups independently selected from $R^{11}$.

Boron esters include boronic acid protecting groups, including moieties derived from diols, for example pinanediol and pinacol to form pinanediol boronic acid ester and the pinacol boronic acid, respectively. Other illustrations of diols useful for deriving boronic acid esters are perfluoropinacol, ethylene glycol, diethylene glycol, 1,2-ethanediol, 1,3-propanediol, 1,2-propanediol, 1,2-butanediol, 1,4-butanediol, 2,3-butanediol, 2,3-hexanediol, 1,2-hexanediol, catechol, 1,2-diisopropylethanediol, 5,6-decanediol, 1,2-dicyclohexylethanediol.

The following abbreviations are used herein:

| | |
|---|---|
| Acm | acetamidomethyl |
| β-Ala, beta-Ala or bAla | 3-aminopropionic acid |
| Boc | t-butyloxycarbonyl |
| CBZ, Cbz or Z | Carbobenzyloxy |
| Dap | 2,3-diaminopropionic acid |
| DCC | dicyclohexylcarbodiimide |
| DIEA | diisopropylethylamine |
| DMAP | 4-dimethylaminopyridine |
| EOE | ethoxyethyl |
| HBTU | 2-(1H-Benzotriazol-1-yl)-1,1,3,3-tetramethyluronium hexafluorophosphate |
| NMeArg or MeArg | α-N-methyl arginine |
| NMeAsp | α-N-methyl aspartic acid |
| NMM | N-methylmorpholine |
| OcHex | O-cyclohexyl |
| OBzl | O-benzyl |
| oSu | O-succinimidyl |
| TBTU | 2-(1H-Benzotriazol-1-yl)-1,1,3,3-tetramethyluronium tetrafluoroborate |
| THF | tetrahydrofuranyl |
| THP | tetrahydropyranyl |
| Tos | tosyl |
| Tr | trityl |

The following conventional three-letter amino acid abbreviations are used herein; the conventional one-letter amino acid abbreviations are not used herein:

| | | |
|---|---|---|
| Ala | = | alanine |
| Arg | = | arginine |
| Asn | = | asparagine |
| Asp | = | aspartic acid |
| Cys | = | cysteine |
| Gln | = | glutamine |
| Glu | = | glutamic acid |
| Gly | = | glycine |
| His | = | histidine |
| Ile | = | isoleucine |
| Leu | = | leucine |
| Lys | = | lysine |
| Met | = | methionine |
| Nle | = | norleucine |
| Phe | = | phenylalanine |
| Phg | = | phenylglycine |
| Pro | = | proline |
| Ser | = | serine |
| Thr | = | threonine |
| Trp | = | tryptophan |
| Tyr | = | tyrosine |
| Val | = | valine |

The compounds of the present invention can be synthesized using standard synthetic methods known to those skilled in the art. For example, one of skill in the art could use the synthetic procedures for making cyclic peptides and for labeling cyclic peptides described in PCT Patent Application Numbers WO 94/22910, WO 94/22494, and US 96/04567, the contents of which are hereby incorporated by reference, to prepare compounds of the present invention. Preferred methods include but are not limited to those methods described below.

Generally, peptides are elongated by deprotecting the α-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference.

The compounds of the invention may also be synthesized using automated peptide synthesizing equipment. In addition to the foregoing, procedures for peptide synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Sythesis" Springer-Verlag, New York (1984), the disclosures of which are hereby incorporated by reference.

The coupling between two amino acid derivatives, an amino acid and a peptide, two peptide fragments, or the cyclization of a peptide can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference.

The $\alpha$-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) *J. Org. Chem.* 45, 1295–1300) chloro or bromomethyl resin, hydroxymethyl resin, and aminomethyl resin. Many of these resins are commercially available with the desired C-terminal amino acid already incorporated.

The $\alpha$-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred $\alpha$-amino protecting group is either Boc or Fmoc. Many amino acid derivatives suitably protected for peptide synthesis are commercially available.

The $\alpha$-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-identified groups. Those skilled in the art will appreciate that the selection and use of appropriate protecting groups for these side chain functionalities will depend upon the amino acid and presence of other protecting groups in the peptide. The selection of such a protecting group is important in that it must not be removed during the deprotection and coupling of the $\alpha$-amino group.

For example, when Boc is chosen for the $\alpha$-amino protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the $\alpha$-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation and cyclization of the peptide is completed all of the protecting groups are removed. For the liquid phase synthesis the protecting groups are removed in whatever manner as dictated by the choice of protecting groups. These procedures are well known to those skilled in the art.

When a solid phase synthesis is used, the peptide should be removed from the resin without simultaneously removing protecting groups from functional groups that might interfere with the cyclization process. Thus, if the peptide is to be cyclized in solution, the cleavage conditions need to be chosen such that a free $\alpha$-carboxylate and a free $\alpha$-amino group are generated without simultaneously removing other protecting groups. Alternatively, the peptide may be removed from the resin by hydrazinolysis, and then coupled by the azide method. Another very convenient method involves the synthesis of peptides on an oxime resin, followed by intramolecular nucleophilic displacement from the resin, which generates a cyclic peptide (Osapay, Profit, and Taylor (1990) *Tetrahedron Letters* 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide can also be accomplished by other acid reagents such as trifluoromethanesulfonic acid/trifluoroacetic acid mixtures.

Unusual amino acids used in this invention can be synthesized by standard methods familiar to those skilled in the art ("The Peptides: Analysis, Sythesis, Biology, Vol. 5, pp. 342–449, Academic Press, New York (1981)). N-Alkyl amino acids can be prepared using procedures described in previously (Cheung et al., (1977) *Can. J. Chem.* 55, 906; Freidinger et al., (1982) *J. Org. Chem.* 48, 77 (1982)), which are incorporated here by reference.

The compounds of the present invention may be prepared using the procedures further detailed below. Representative materials and methods that may be used in preparing the compounds of the invention are described further below.

Manual solid phase peptide synthesis was performed in 25 mL polypropylene filtration tubes purchased from BioRad Inc., or in 60 mL hour-glass reaction vessels purchased from Peptides International. Oxime resin (substitution level=0.96 mmol/g) was prepared according to published procedures (DeGrado and Kaiser (1980) *J. Org. Chem.* 45, 1295), or was purchased from Novabiochem (substitution level=0.62 mmol/g). All chemicals and solvents (reagent grade) were used as supplied from the vendors cited without further purification. t-Butyloxycarbonyl (Boc) amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DIEA) were purchased from Aldrich Chemical Company. Dimethylformamide (DMF), ethyl acetate, chloroform (CHCl$_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were commercially obtained. Absolute ethanol was obtained from Quantum Chemical Corporation.

Other features of the invention will become apparent in the course of the following descriptions of exemplary embodiments which are given for illustration of the invention and are not intended to be limiting thereof.

EXAMPLES

Example 1

Preparation of Cyclo-[D-Val-NMeArg-Gly-Asp-Dap-Cys(Acm)]

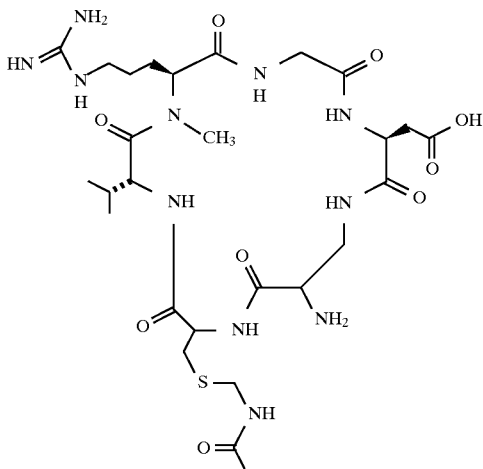

Cyclic Peptide Intermediate Cyclo-[D-Val-NMeArg (Tos)-Gly-Asp(OBzl)-Dap(Cbz)-Cys(Acm)] (A)

The cyclic hexapeptide intermediate (A) was prepared by manual solid phase peptide synthesis using Boc-teabag chemistry (Houghton, 1985) on a p-nitrobenzophenone oxime solid support (DeGrado 1982, Scarr and Findeis, 1990). The 5.0 cm×5.0 cm teabags were made from 0.75 mm mesh polypropylene filters (Spectra Filters) and filled with 0.5 g of the oxime resin. In all four cases the synthesis of the protected tripeptide-resin intermediate was achieved by first coupling Boc-Cys(Acm)-OH to he oxime resin (substitution 0.69 mmol/g). Attachment of Boc-Cys(Acm)-OH onto the oxime resin was achieved by using five equivalents of the amino acid, HBTU and excess of Diisopropylamine (DIPEA) in DMF. Coupling of the first amino acid occurred over four days. Removal of the Boc group (25% TFA in CH$_2$Cl$_2$) and quantitative analysis of amine groups using the picric acid assay gave a loading yield of 0.434 mmol/g. Unreacted oxime groups on the resin were then capped with a solution of DIPEA and trimethyacetyl chloride in DMF. Subsequent washings (DMF 3x, CH$_2$Cl$_2$ 9x) and coupling of the other amino acids were performed in a similar manner utilizing a polypropylene reactor that was shaken on an oscillator. Coupling of the subsequent amino acids Boc-Dap (Cbz)-OH, Boc-Asp(OBzl)-OH, Boc-Gly, Boc-N-Me-Asp (Tos)-OH, Boc-D-Val-OH on the resin were achieved by overnight shaking, and the coupling yields for each newly added amino acid was determined using the picric acid (Stewart and Martin, 19xx) assay.

After the desired hexapeptide was assembled, the Boc-group on the terminal amino acid (D-Val) was removed from resin-bound peptide using TFA. After subsequent washes and neutralization using DIPEA the resin-bound peptide was incubated with equimolar amounts of glacial acetic acid and in DMF. This,mixture was heated in an oil bath (50° C.) for 72 hr in a N$_2$ atmosphere. Thereafter the resin was filtered off and washed with DMF (3×5 ml). The solvent was then removed in vacuo and the residue lyophilized in a 50% MeCN:Water solution to yield the crude product.

Deprotection of Cyclo-[D-Val-NMeArg(Tos)-Gly-Asp(OBzl)-Dap (Cbz)-Cys(Acm)]

Deprotection of the Tosylate group on arginine, the OBzl group on aspartic acid and the Cbz- group on the N-terminus of diaminopropionic acid was achieved simultaneously, utilizing a TFMSA/TFA mixture. Briefly, the protected cyclic peptide (100 mg) was dissoved in TFA (2 ml), and stirred under N$_2$ at ~−10° C. Triflic acid (2 ml) was added to this dropwise and the temperature maintained at ~−10° C. To this was added 0.4 ml of anisole and the mixture stirred at ~−10° C. for another 3 hours. Subsequently 200 ml of cold diethyl ether was added to the reaction mixture and the temperature was lowered to ~−35° C. The mixture was stirred under these conditions for 0.5 hours, upon which the temperature was further lowered to ~−78° C. and stirred for another 1.5 hours. The white precipitate formed was filtered through a medium frit funnel and washed several times with cold ether. The precipitate was transferred to 100 ml flask and dissolved in 20 ml of a water:acetone (1:1) mixture. This solution was treated with 1.5 ml of Bio-Rad-AG 1×2 (Acetate) prewashed resin. The mixture was stirred for 30 mins. upon which the pH changed from 1.0 to 4.5. The solution was filtered, the resin washed (3×5 ml) with water and the filtrate lyophilized.

Purification of the crude product was achieved by preparative HPLC(Method used a Rainin instrument and a Vydac C18 column (5 cm×25 cm) at a flow rate of 15 mL/min with a gradient mobile phase from 2% B to 50% B over 30 min (A=100% water with 0.1% TFA and B=50% aqueous acetonitrile with 0.1% TFA) monitored at 220 nm. Ret. time (min): 18.1. The compound was analysed using the method indicated: analytical HPLC method used a Hewlett Packard Model 1050 instrument and a Vydac C18 column (4.6 mm×25 cm) at a flow rate of 1 mL/min with a gradient mobile phase from 2% B to 100% B over 45 min (A=100% water with 0.1% TFA and B=90% aqueous acetonitrile with 0.1% TFA) monitored at 220 nm. Ret. time (min): 9.39.

HRMS-FAB m/z calcd. for C$_{27}$H$_{47}$N$_{11}$O$_9$S+H: 702.3357; Found: 702.3370.

Example 2

Preparation of Cyclo-[D-Val-NMeArg-Gly-Asp-Dap(EOE-Mercaptoacetyl)-Cys(Acm)]

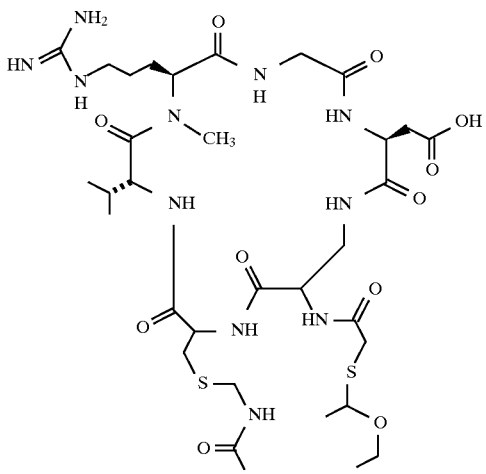

To a stirring suspension of the title compound of Example 1 (11 mg, 0.012 mmol) in 7 ml of anhydrous dimethylformamide containing diisopropylethylamine (0.01 ml, 0.0472 mmol) was added N-hydroxysuccinimidyl S-(1-ethoxyethyl) mercapto-acetate (1.5 mg, 0.0059 mmol) dissolved in 5 ml of anhydrous dimethyl-formamide. The reaction mixture was stirred for 3 hr at RT under a N2 atmosphere, upon which the solution was concentrated to a viscous oil under vacuum. The oil was dissolved in 50% tgaqueous acetonitrile and lyophilized overnight to yield the crude product in the form of its trifluoroacetate salt (yield, 90%, 12 mg, 0.0124 mmol).

Purification of the crude product was achieved by prep. HPLC (Method used a Rainin instrument and a Vydac C18 column (5 cm×25 cm) at a flow rate of 15 mL/min with a gradient mobile phase from 2% B to 50% B over 30 min (A=100% water with 0.1% TFA and B=50% aqueous acetonitrile with 0.1% TFA) monitored at 220 nm. Ret. time (min): 18.1. Yield 6.8 mg of the TFA salt. The compound was analyzed using the method indicated: Analytical HPLC method us ed a Hewlett Packard Model 1050 instrument and a Vydac C18 column (4.6 mm×25 cm) at a flow rate of 1 mL/min in with a gradient mobile phase from 2% B to 100% B over 45 min (A=100% water with 0.1% TFA and B=90% aqueous acetonitrile with 0.1% TFA) monitored at 220 nm. Ret. time (min): 11.96.

HRMS-FAB: m/z calcd. for $C_{33}H_{57}N_{11}O_{11}S_{2+H}$: 848.3759; Found: 848.3770.

Example 3

Preparation of 99m-Tc(O)-Cyclo-[D-Val-NMeArg-Gly-Asp-Dap(EOE-Mercaptoacety)-Cys(Acm)]

An acidified solution of the peptide was prepared by adding 0.16 ml of 0.2M hydrochloric acid-glacial acetic acid (14:2 ratio) to 0.6 ml of Cyclo-[D-Val-NMeArg-Gly-Asp-Dap(EOE-metcaptoacety)-Cys(Acm)] (0.2 mg, 0.0002 mmole freshly dissolved in 1.0 ml water). Then 0.5 ml of this solution was added to 1.1 ml of $^{99m}$Tc-gluconate (the $^{99m}$Tc-gluconate was prepared from 0.12 mg $SnCl_2.2H_2O$, 5.0 mg of sodium gluconate at pH 6.1–6.3 and 87 mCi of [$^{99m}$Tc]pertechnetate. The reaction mixture was then heated at 80° C. for 20 min followed by cooling at RT. After cooling ~2 minutes, 20 μL of the solution was analyzed by the HPLC described below.

The radiochemical purity (% RCP) of the resulting complex was determined using HPLC. The method used a Hewlett Packard 1050 instrument and a Vydac C18 column (4.6 mm×25 cm) at a flow rate of 1 mL/min with a gradient mobile phase from 100% A (10 mM phosphate buffer, pH 6), to 30% B (acetonitrile) at 15 min and 75% B at 25 min. RCP values were obtained at 0, 1, 3 and 6 hours post-heating of the kits (RCP>92%, n=2).

Some examples of the present invention which can be prepared by the above described synthetic procedures are shown below in Table 1.

| Ex. | $R^1$ | $R^2$ |
|---|---|---|
| 1 | (Acm)SCH$_2$ | H |
| 2 | (Acm)SCH$_2$ | (EOE)SCH$_2$C(=O) |
| 3 | (Acm)SCH$_2$ | (Acm)SCH$_2$C(=O) |
| 4 | (Acm)SCH$_2$ | (THF)SCH$_2$C(=O) |
| 5 | (Acm)SCH$_2$ | (THP)SCH$_2$C(=O) |
| 6 | (Acm)SCH$_2$ | H$_2$NCH$_2$C(=O) |
| 7 | (Acm)SCH$_2$ | 2-hydroxyphenylmethyl |
| 8 | (Acm)SCH$_2$ | (Acm)SC(CH$_3$)$_2$C(=O) |
| 9 | (Acm)SCH$_2$ | (EOE)SC(CH$_3$)$_2$C(=O) |
| 10 | (EOE)SCH$_2$ | H |
| 11 | (EOE)SCH$_2$ | (EOE)SCH$_2$C(=O) |
| 12 | (EOE)SCH$_2$ | (Acm)SCH$_2$C(=O) |
| 13 | (EOE)SCH$_2$ | (THF)SCH$_2$C(=O) |
| 14 | (EOE)SCH$_2$ | (THP)SCH$_2$C(=O) |
| 15 | (EOE)SCH$_2$ | H$_2$NCH$_2$C(=O) |
| 16 | (EOE)SCH$_2$ | 2-hydroxyphenylmethyl |
| 17 | (EOE)SCH$_2$ | (Acm)SC(CH$_3$)$_2$C(=O) |
| 18 | (EOE)SCH$_2$ | (EOE)SC(CH$_3$)$_2$C(=O) |
| 19 | (THF)SCH$_2$ | H |
| 20 | (THF)SCH$_2$ | (EOE)SCH$_2$C(=O) |
| 21 | (THF)SCH$_2$ | (Acm)SCH$_2$C(=O) |
| 22 | (THF)SCH$_2$ | (THF)SCH$_2$C(=O) |
| 23 | (THF)SCH$_2$ | (THP)SCH$_2$C(=O) |
| 24 | (THF)SCH$_2$ | H$_2$NCH$_2$C(=O) |
| 25 | (THF)SCH$_2$ | 2-hydroxyphenylmethyl |
| 26 | (THF)SCH$_2$ | (Acm)SC(CH$_3$)$_2$C(=O) |
| 27 | (THF)SCH$_2$ | (EOE)SC(CH$_3$)$_2$C(=O) |
| 28 | (THP)SCH$_2$ | H |
| 29 | (THP)SCH$_2$ | (EOE)SCH$_2$C(=O) |
| 30 | (THP)SCH$_2$ | (Acm)SCH$_2$C(=O) |
| 31 | (THP)SCH$_2$ | (THF)SCH$_2$C(=O) |
| 32 | (THP)SCH$_2$ | (THP)SCH$_2$C(=O) |
| 33 | (THP)SCH$_2$ | H$_2$NCH$_2$C(=O) |
| 34 | (THP)SCH$_2$ | 2-hydroxyphenylmethyl |
| 35 | (THP)SCH$_2$ | (Acm)SC(CH$_3$)$_2$C(=O) |
| 36 | (THP)SCH$_2$ | (EOE)SC(CH$_3$)$_2$C(=O) |

Utility

The radiolabeled compounds of the present invention are useful as radiopharmaceuticals for imaging a thrombus such as may be present in a patient with unstable angina, myocardial infarction, transient ischemic attack, stroke, atherosclerosis, diabetes, thrombophlebitis, pulmonary emboli, or prosthetic cardiac devices such as heart valves, and thus may be used to diagnose such present or potential disorders. The patient may be any type of a mammal, but is preferably a human. The radiolabeled compounds may be used alone, or may be employed as a composition with a radiopharmaceutically acceptable carrier, and/or in combination with other diagnostic or therapeutic agents. Suitable radiopharmaceuticals carriers and suitable amounts thereof are well known in the art, and can be found in, for example, Remington's Pharmaceutical Sciences, Gennaro, A. R., ed., Mack Publishing Company, Easton, Pa. (1985), and The United States Pharmacopia—The National Formulary, 22nd Revision, Mack Printing Company, Easton, Pa. (1990), standard reference texts in the pharmaceutical field. Other materials may be added, as convenient, to stabilize the composition, as those skilled in the art will recognize, including antioxidizing agents such as sodium bisulfite, sodium sulfite ascorbic acid, gentisic acid or citric acid (or their salts) or sodium ethylenediamine tetraacetic acid (sodium EDTA), as is well known in the art. Such other materials, as well as suitable amounts thereof, are also described in Remington's Pharmaceutical Sciences and The United States Pharmacopia—The National Formulary, cited above.

The present invention also includes radiopharmaceutical kits containing the labeled compounds of the present invention. Such kits may contain the labeled compounds in sterile lyophilized form, and may include a sterile container of a radiopharmaceutically acceptable reconstitution liquid. Suitable reconstitution liquids are disclosed in Remington's Pharmaceutical Sciences and The United States Pharmacopia—The National Formulary, cited above. Such kits may alternatively contain a sterile container of a composition of the radiolabeled compounds of the invention. Such kits may also include, if desired, other conventional kit components, such as, for example, one or more carriers, one or more additional vials for mixing. Instructions, either as inserts or labels, indicating quantities of the labeled compounds of the invention and carrier, guidelines for mixing these components, and protocols for administration may also be included in the kit. Sterilization of the containers and any materials included in the kit and lyophilization (also referred to as freeze-drying) of the labeled compounds of the invention may be carried out using conventional sterilization and lyophilization methodologies known to those skilled in the art.

Another aspect of the present invention is diagnostic kits for the preparation of radiopharmaceuticals. Diagnostic kits of the present invention comprise one or more vials containing the sterile, non-pyrogenic, formulation comprised of a predetermined amount of a reagent of formula (I), a reducing agent, and optionally a solubilization aid or other components such as transfer ligands, buffers, lyophilization aids, stabilization aids, and bacteriostats. The inclusion of one or more optional components in the formulation will frequently improve the ease of synthesis of the radiopharmaceutical by the practising end user, the ease of manufacturing the kit, the shelf-life of the kit, or the stability and shelf-life of the radiopharmaceutical. The improvement achieved by the inclusion of an optional component in the formulation must be weighed against the added complexity of the formulation and added cost to manufacture the kit. The one or more vials that contain all or part of the formulation can independently be in the form of a sterile solution or a lyophilized solid.

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly (oxyethylene) block copolymers (Pluronics) and lecithin. Preferred solubilizing aids are polyethylene glycol, and Pluronics.

Buffers useful in the preparation of radiopharmaceuticals and in diagnostic kits useful for the preparation of said radiopharmaceuticals include but are not limited to phosphate, citrate, sulfosalicylate, and acetate. A more complete list can be found in the United States Pharmacopeia.

Lyophilization aids useful in the preparation diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Bacteriostats useful in the preparation of radiopharmaceuticals and in diagnostic kits useful for the preparation of said radiopharmaceuticals include but are not limited to benzyl alcohol, benzalkonium chloride, chlorobutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The predetermined amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practising end user can synthesize the radiopharmaceutical and have a high degree of certainty that the radiopharmaceutical can be safely injected into a patient and will provide diagnostic information about the disease state of that patient.

The diagnostic kits of the present invention will also contain written instructions for the practising end user to follow to synthesize the radiopharmaceuticals. These instructions may be affixed to one or more of the vials or to the container in which the vial or vials are packaged for shipping or may be a separate insert, termed the package insert.

To carry out one of the methods of the present invention, the radiolabeled compounds are generally administered intravenously, by bolus injection, although they may be administered by any means that produces contact of the compounds with platelets. Suitable amounts for administration will be readily ascertainable to those skilled in the art, once armed with the present disclosure. The dosage administered will, of course, vary depending up such known factors as the particular compound administered, the age, health and weight or the nature and extent of any symptoms experienced by the patient, the amount of radiolabeling, the particular radionuclide used as the label, the rate of clearance of the radiolabeled compounds from the blood. Acceptable ranges for administration of radiolabeled materials are tabulated, for example, in the Physicians Desk Reference (PDR) for Nuclear Medicine, published by Medical Exonomics Company, a well-known reference text. A discussion of some of the aforementioned considerations is provided in Eckelman et al., J. Nucl. Med., Vol. 209, pp. 350–357 (1979). By way of general guidance, a dosage range of the radiolabeled compounds of the invention may be between about 1 and about 40 mCi.

Once the radiolabeled compounds of the invention are administered, the presence of thrombi may be visualized using a standard radioscintographic imaging system, such as, for example, a gamma camera or a computed tomographic device, and thromboembolic disorders detected. Such imaging systems are well known in the art, and are discussed, for example, in Macovski, A., Medical Imaging Systems, Information and Systems Science Series, Kailath, T., ed., Prentice-Hall, Inc., Englewood Cliffs, N.J. (1983). Particularly preferred are single-photon emission computed tomography (SPECT) and positron emission tomography (PET). Specifically, imaging is carried out by scanning the entire patient, or a particular region of the patient suspected of having a thrombus formation, using the radioscintographic system, and detecting the radioisotope signal. The detected signal is then converted into an image of the thrombus by the system. The resultant images should be read by an experienced observer, such as, for example, a nuclear medicine physician. The foregoing process is referred to herein as "imaging" the patient. Generally, imaging is carried out about 1 minute to about 48 hours following administration of the radiolabeled compound of the invention. The precise timing of the imaging will be dependant upon such factors as the half-life of the radioisotope employed, and the clearance rate of the compound administered, as will be readily apparent to those skilled in the art. Preferably, imaging is carried out between about 1 minute and about 4 hours following administration.

The advantage of employing the radiolabeled compounds of the invention, which have the ability to localize specifically and with high affinity in thrombi, to detect the presence of thrombi and/or to diagnose thromboembolic disorders in a patient, will be readily apparent to those skilled in the art, once armed with the present disclosure.

Arteriovenous Shunt Model

Adult mongrel dogs of either sex (9–13 kg) were anesthetized with pentobarbital sodium (35 mg/kg,i.v.) and ventilated with room air via an endotracheal tube (12 strokes/min,25 ml/kg). For arterial pressure determination, the left carotid artery was cannulated with a saline-filled polyethylene catheter (PE-240) and connected to a Statham pressure transducer (P23ID; Oxnard,Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. A jugular vein was cannulated (PE-240) for drug administration. The both femoral arteries and femoral veins were cannulated with silicon treated (Sigmacote, Sigma Chemical Co. St Louis, Mo.), saline filled polyethylene tubing (PE-200) and connected with a 5 cm section of silicon treated tubing (PE-240) to form an extracorporeal arterio-venous shunts (A-V). Shunt patency was monitored using a doppler flow system (model VF-1, Crystal Biotech Inc, Hopkinton, Mass.) and flow probe (2–2.3 mm, Titronics Med. Inst., Iowa City, Iowa) placed proximal to the locus of the shunt. All parameters were monitored continuously on a polygraph recorder (model 7D Grass) at a paper speed of 10 mm/min or 25 mm/sec.

On completion of a 15 min post surgical stabilization period, an occlusive thrombus was formed by the introduction of a thrombogenic surface (4–0 braided silk thread, 5 cm in length, Ethicon Inc., Somerville, N.J.) into the shunt one shunt with the other serving as a control. Two consecutive 1 hr shunt periods were employed with the test agent administered as an infusion over 5 min beginning 5 min before insertion of the thrombogenic surface. At the end of each 1 hr shunt period the silk was carefully removed and weighed and the % incorporation determined via well counting. Thrombus weight was calculated by subtracting the weight of the silk prior to placement from the total weight of the silk on removal from the shunt. Arterial blood was withdrawn prior to the first shunt and every 30 min thereafter for determination of blood clearance, whole blood collagen-induced platelet aggregation, thrombin-induced platelet degranulation (platelet ATP release), prothrombin time and platelet count. Template bleeding time was also performed at 30 min intervals.

Canine Deep Vein Thrombosis Model

This model incorporates the triad of events (hypercoagulatible state, period of stasis, low shear environment) essential for the formation of a venous fibrin-rich actively growing thrombus. The procedure was as follows: Adult mongrel dogs of either sex (9–13 kg) were anesthetized with pentobarbital sodium (35 mg/kg,i.v.) and ventilated with room air via an endotracheal tube (12 strokes/min, 25 ml/kg). For arterial pressure determination, the right femoral artery was cannulated with a saline-filled polyethylene catheter (PE-240) and connected to a Statham pressure transducer (P23ID; Oxnard,Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. The right femoral vein was cannulated (PE-240) for drug administration. A 5 cm segment of both jugular veins was isolated, freed from fascia and circumscribed with silk suture. A microthermister probe was placed on the vessel which serves as an indirect measure of venous flow. A balloon embolectomy catheter was utilized to induce the 15 min period of stasis during which time a hypercoagulatible state was then induced using 5 U thrombin (American Diagnosticia, Greenwich Conn.) administered into the occluded segment. Fifteen minutes later, flow was reestablished by deflating the balloon. The agent was infused during the first 5 min of reflow and the rate of incorporation monitored using gamma scintigraphy.

Platelet Aggregation Assay

Canine blood was collected into 10 ml citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 $\mu$l of PRP was added to each micro test tube, and transmittance was set to 0%. 20 $\mu$l of various agonists (ADP, collagen, arachidonate, epinephrine, thrombin) were added to each tube, and the aggregation profiles were plotted (% transmittance versus time). The results were expressed as % inhibition of agonist-induced platelet aggregation. For the $IC_{50}$ evaluation, the test compounds were added at various concentrations prior to the activation of the platelets.

Platelet-Fibrinogen Binding Assay

Binding of $^{125}$I-fibrinogen to platelets was performed as described by Bennett et al. (1983) Proc. Natl. Acad. Sci.

U.S.A. 80: 2417–2422, with some modifications as described below. Human PRP (h-PRP) was applied to a Sepharose column for the purification of platelet fractions. Aliquots of platelets (5×10⁸ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated, platelets was separated from the free form by centrifugation and then counted on a gamma counter. For an $IC_{50}$ evaluation, the test compounds were added at various concentrations prior to the activation of the platelets.

The novel cyclic glycoprotein IIb/IIIa compounds of the invention may also possess thrombolytic efficacy, that is, they are capable of lysing (breaking up) already formed platelet-rich fibrin blood clots, and thus may useful in treating a thrombus formation, as evidenced by their activity in the tests described below. Preferred cyclic compounds of the present invention for use in thrombolysis would include those compounds having an $IC_{50}$ value (that is, the molar concentration of the cyclic compound capable of achieving 50% clot lysis) of less than about 1 mM, more preferably an $IC_{50}$ value of less than about 0.1 mM, even more preferably an $IC_{50}$ value of less than about 0.01 mM, still more preferably an $IC_{50}$ value of less than about 0.001 mM, and most preferably an $IC_{50}$ value of about 0.0005 mM.

$IC_{50}$ determinations may be made using a standard thrombolysis assay, as described below. Another class of preferred thrombolytic compounds of the invention would include those compounds which have a Kd of <100 nM, preferably <10 nM, most preferably 0.1 to 1.0 nM.

Thrombolytic Assay

Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500×g at room temperature, and platelet rich plasma (PRP) was removed. To the PRP was then added $1×10^{-3}$M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

The disclosures of each patent and publication cited in this document are hereby incorporated herein by reference, in their entirety.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A reagent for preparing a radiopharmaceutical, wherein the reagent is of formula (I):

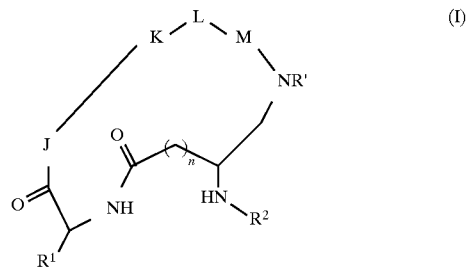

or a pharmaceutically acceptable salt or prodrug form thereof, wherein:

R' is H or $C_1$–$C_8$ alkyl;

$R^1$ is selected from the group: H, $C_1$–$C_4$ alkyl substituted with 0–3 $R^{20}$, $C_{6-10}$ aryl substituted with 0–3 $R^{20a}$, $C_{3-8}$ cycloalkyl substituted with 0–3 $R^{20a}$, —$C_{6-10}$ aryl($C_{1-4}$ alkyl) substituted with 0–3 $R^{20a}$, and a 5–10-membered heterocyclic ring system, containing 1–4 heteroatoms independently selected from N, S, and O, substituted with 0–1 $R^{20a}$;

$R^{20}$ is independently selected at each occurrence from the group:
$R^{20a}$;
$C_{6-10}$ aryl substituted with 0–1 $R^{20a}$; and,
a 5–10-membered heterocyclic ring system, containing 1–4 heteroatoms independently selected from N, S, and O, substituted with 0–1 $R^{20a}$;

$R^{20a}$ is independently selected at each occurrence from the group: —CN, —$CO_2R^{21}$, —C(=O)$R^{21a}$, C(=O)$CH_2OR^{21}$, C(=O)N$R^{22}$C(=O)$R^{21a}$, C(=O)$OCH_2CO_2H$, C(=O)N$R^{23}R^{24}$, —C(=O)N($R^{22})_2$, —$CH_2OR^{21}$, —OC(=O)$R^{21a}$, —OC(=O)O$R^{21a}$, —O$R^{21a}$, —OC(=O)N($R^{22})_2$, —N$R^{22}$C(=O)$R^{21a}$, —N$R^{22}$C(=O)O$R^{21}$, —N$R^{22}$C(=O)N($R^{22})_2$, —N($R^{22})_2$, =NO$R^{21}$, —C(=O)NHO$R^{21}$, —C(=O)NHN$R^{22}R^{22}$, —OCH$_2$CO$_2$H, N$R^{23}R^{24}$, —N$R^{22}SO_2$N($R^{22})_2$, —N$R^{22}SO_2R^{21b}$, —$SO_3$H, —$SO_2R^{21b}$, —$SR^{21}$, —S(=O)$R^{21b}$, —$SO_2$N($R^{22})_2$, SCH$_2$N$R^{22}$C(=O)$R^{21}$, SH, S(Pg), =O, OH, P$R^{25}R^{26}$, P(O)$R^{25}R^{26}$, P(S)$R^{25}R^{26}$, P(N$R^{27}$)$R^{25}R^{26}$; and a 5–10-membered heterocyclic ring system containing 1–4 heteroatoms independently selected from N, S, and O;

$R^{21}$ is independently selected at each occurrence from the group: H, $C_1$–$C_6$ alkyl, phenyl, benzyl, and trifluoromethyl;

$R^{21a}$ is independently selected at each occurrence from the group: H, $C_1$–$C_6$ alkyl, phenyl, benzyl, OH, $C_1$–$C_6$ alkoxy, halide, and trifluoromethyl;

$R^{21b}$ is independently selected at each occurrence from the group: $C_1$–$C_6$ alkyl, phenyl, benzyl, $C_1$–$C_6$ alkoxy, and trifluoromethyl;

$R^{22}$ is independently selected at each occurrence from the group: H, $C_1$–$C_6$ alkyl, phenyl, benzyl, cyano, and trifluoromethyl;

$R^{23}$, $R^{24}$, $R^{25}$, $R^{26}$, and $R^{27}$ are each independently selected at each occurrence from the group:

hydrogen;
C$_{1-10}$ alkyl substituted with 0–3 R$^{40}$;
C$_{6-10}$ aryl substituted with 0–3 R$^{40}$;
C$_{3-8}$ cycloalkyl substituted with 0–3 R$^{40}$;
heterocyclyl-C$_{1-6}$ alkyl substituted with 0–3 R$^{40}$, wherein the heterocycle is selected from the group: pyridine, pyrazine, proline, furan, thiofuran, thiazole, and diazine;
—C$_{6-10}$ aryl(C$_{1-6}$ alkyl) substituted with 0–3 R$^{40}$;
—C$_{1-6}$ alkyl(C$_{6-10}$ aryl) substituted with 0–3 R$^{40}$; and
an electron, provided that when one of R$^{23}$ or R$^{24}$ is an electron, then the other is also an electron, and provided that when one of R$^{25}$ or R$^{26}$ is an electron, then the other is also an electron;
R$^{40}$ is selected from the group: C$_{1-6}$ alkyl, phenyl, halo, —NO$_2$, —CN, —CO$_2$R$^{21}$, —C(=O)R$^{21a}$, C(=O)N(R$^{22}$)$_2$, —CH$_2$R$^{21}$, —OC(=O)R$^{21a}$, —OR$^{21a}$, —NR$^{22}$C(=O)R$^{21a}$, —N(R$^{22}$)$_2$, —C(=O)NHOR$^{21}$, —C(=O)NHNR$^{22}$R$^{22}$, —NR$^{22}$SO$_2$R$^{21b}$, —SO$_3$H, —SO$_2$R$^{21b}$, —SR$^{21}$, —S(=O)R$^{21b}$, and —SO$_2$N(R$^{22}$)$_2$;
R$^2$ is independently selected at each occurrence from the group: H, C$_1$–C$_4$ alkyl substituted with 0–3 R$^{41}$, C$_{6-10}$ aryl substituted with 0–3 R$^{41a}$, C$_{3-8}$ cycloalkyl substituted with 0–3 R$^{41a}$, —C$_{6-10}$ aryl(C$_{1-4}$ alkyl) substituted with 0–3 R$^{41a}$, and a 5–10-membered heterocyclic ring system, containing 1–4 heteroatoms independently selected from N, S, and O, substituted with 0–1 R$^{20a}$;
R$^{41}$ is independently selected at each occurrence from the group:
R$^{41a}$;
C$_{6-10}$ aryl substituted with 0–1 R$^{41a}$; and,
a 5–10-membered heterocyclic ring system, containing 1–4 heteroatoms independently selected from N, S, and O, substituted with 0–1 R$^{41a}$;
R$^{41a}$ is independently selected at each occurrence from the group: NR$^{23}$R$^{24}$, =S, SH, S(Pg), =O, OH, PR$^{25}$R$^{26}$, P(O)R$^{25}$R$^{26}$, P(S)R$^{25}$R$^{26}$, and P(NR$^{27}$)R$^{25}$R$^{26}$;
provided that at least one of R$^1$ and R$^2$ contains at least one group selected from NR$^{23}$R$^{24}$, S, =S, SH, S(Pg), O, =O, OH, PR$^{25}$R$^{26}$, P(O)R$^{25}$R$^{26}$, P(S)R$^{25}$R$^{26}$, and P(NR$^{27}$)R$^{25}$R$^{26}$;
J is β-Ala or an L-isomer or D-isomer amino acid of the formula —N(R$^3$)C(R$^4$)(R$^5$)C(=O)—;
R$^3$ is H or C$_1$–C$_8$ alkyl;
R$^4$ is H or C$_1$–C$_3$ alkyl;
R$^5$ is independently selected from the group: H, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, =NOR$^{13}$, —B(R$^{34}$)(R$^{35}$), —OCH$_2$CO$_2$H, 2-(1-morpholino)ethoxy, —SC(=NH)NHR$^{13}$, N$_3$, —Si(CH$_3$)$_3$, (C$_1$–C$_5$ alkyl)NHR$^{16}$;
C$_1$–C$_8$ alkyl substituted with 0–2 R$^{11}$;
C$_2$–C$_8$ alkenyl substituted with 0–2 R$^{11}$;
C$_2$–C$_8$ alkynyl substituted with 0–2 R$^{11}$;
C$_3$–C$_{10}$ cycloalkyl substituted with 0–2 R$^{11}$;
aryl substituted with 0–2 R$^{12}$;
a 5–10-membered heterocyclic ring system containing 1–4 heteroatoms independently selected from N, S, and O, said heterocyclic ring being substituted with 0–2 R$^{12}$;

—C$_0$–C$_6$ alkyl-X;
—(CH$_2$)$_{q'}$-phenyl-(CH$_2$)$_{q'}$—X, wherein substitution on the phenyl is 1,4;
—CH$_2$-cyclohexyl-CH$_2$X, wherein substitution on the cyclohexyl is 1,4; and,
—(CH$_2$)$_m$S(O)$_p$(CH$_2$)$_2$X;
R$^3$ and R$^4$ may also be taken together to form —CH$_2$((CH$_2$)$_n$NHC(=NR$^{13}$)N(R$^{13}$)$_2$)CH$_2$—
R$^3$ and R$^5$ can alternatively be taken together to form —(CH$_2$)$_t$— or —CH$_2$S(O)$_p$C(CH$_3$)$_2$—;
R$^4$ and R$^5$ can alternatively be taken together to form —(CH$_2$)$_u$—;
K is a D-isomer or L-isomer amino acid of the formula —N(R$^6$)CH(R$^7$)C(=O)—;
R$^6$ is H or C$_1$–C$_8$ alkyl;
R$^7$ is selected from the group:
—C$_1$–C$_7$ alkyl-X;
—(CH$_2$)$_{q'}$-phenyl-(CH$_2$)$_{q'}$—X, wherein substitution on the phenyl is 1,3 or 1,4;
—(CH$_2$)$_{q'}$-cyclohexyl-(CH$_2$)$_{q'}$—X, wherein substitution on the cyclohexyl is 1,3 or 1,4;

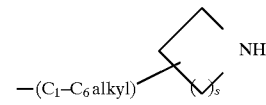

—(CH$_2$)$_m$O—(C$_1$–C$_4$ alkyl)-X; and,
—(CH$_2$)$_m$S(O)$_{p'}$—(C$_1$–C$_4$ alkyl)-X;
X is selected from the group: NHC(=NR$^{13}$)N(R$^{13}$)R$^{13}$, —N(R$^{13}$)R$^{13}$, —C(=NH)(NH$_2$), —SC(=NH)—NH$_2$, —NH—C(=NH)(NHCN), —NH—C(=NCN)(NH$_2$), and —NH—C(=N—OR$^{13}$)(NH$_2$);
R$^6$ and R$^7$ can alternatively be taken together to form

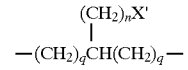

X' is —NH$_2$ or NHC(=NR$^{13}$)N(R$^{13}$)R$^{13}$;
L is —Y(CH$_2$)$_v$C(=O)—;
Y is NH, N(C$_1$–C$_3$ alkyl), O, or S;
M is a D-isomer or L-isomer amino acid of the formula

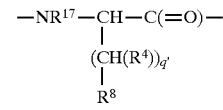

R$^{17}$ is H or C$_1$–C$_3$ alkyl;
R$^8$ is selected from the group: —CO$_2$R$^{13}$, —SO$_3$R$^{13}$, —SO$_2$NHR$^{14}$, —B(R$^{34}$)(R$^{35}$), —NHSO$_2$CF$_3$, —CONHNSO$_2$CF$_3$, —PO(OR$^{13}$)$_2$, —PO(OR$^{13}$)R$^{13}$, —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$, and —SO$_2$NH-heteroaryl, said heteroaryl being 5–10-membered and having 1–4 heteroatoms selected independently from N, S, and O;
R$^{11}$ is independently selected at each occurrence from the group: =O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$—NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy, C$_{1-6}$ alkyl, C$_2$–C$_4$ alkenyl, C$_3$–C$_6$ cycloalkyl, C$_3$–C$_6$ cycloalkylmethyl, C$_{2-6}$ alkoxy-C$_{1-6}$ alkyl, C$_3$–C$_6$ cycloalkoxy, and C$_{1-4}$ alkyl, said C$_{1-4}$ alkyl being substituted with 1–5 groups selected independently from the group: —NR$^{13}$R$^{14}$, —CF$_3$, NO$_2$, —SO$_2$R$^{13a}$, —S(=O)R$^{13a}$, C$_{6-10}$ aryl substituted with 0–2 R$^{12}$, and a 5–10-membered heterocyclic ring system containing 1–4 heteroatoms independently selected from N, S, and O, said heterocyclic ring being substituted with 0–2 R$^{12}$;

R$^{12}$ is independently at each occurrence selected from the group: phenyl, benzyl, phenethyl, phenoxy, benzyloxy, halogen, hydroxy, nitro, cyano, C$_1$–C$_5$ alkyl, C$_3$–C$_6$ cycloalkyl, C$_3$–C$_6$ cycloalkylmethyl, C$_{6-10}$ aryl-C$_{1-6}$ alkyl, C$_1$–C$_5$ alkoxy, —CO$_2$R$^{13}$, —C(=O)NHOR$^{13a}$, —C(=O)NHN(R$^{13}$)$_2$, =NOR$^{13}$, —B(R$^{34}$)(R$^{35}$), C$_3$–C$_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, C$_2$–C$_6$ alkoxyalkyl, methylenedioxy, ethylenedioxy, C$_1$–C$_4$ haloalkyl, C$_1$–C$_4$ haloalkoxy, C$_1$–C$_4$ alkylcarbonyloxy, C$_1$–C$_4$ alkylcarbonyl, C$_1$–C$_4$ alkylcarbonylamino, —OCH$_2$CO$_2$H, 2-(1-morpholino)ethoxy, and C$_{1-4}$ alkyl, said C$_{1-4}$ being substituted with 1–5 groups selected independently from the group: —N(R$^{13}$)$_2$, —CF$_3$, NO$_2$, and —S(=O)R$^{3a}$;

R$^{13}$ and R$^{13a}$ are selected independently at each occurrence from the group: H, C$_1$–C$_{10}$ alkyl, C$_3$–C$_{10}$ cycloalkyl, C$_{1-4}$ alkyl-C$_{3-6}$ cycloalkyl, C$_{6-10}$ aryl, —C$_{1-10}$ alkyl-C$_{6-10}$ aryl, and C$_{1-6}$ alkoxy-C$_{1-6}$ alkyl;

when two R$^{13}$ groups are bonded to a single N, said R$^{13}$ groups may alternatively be taken together to form —(CH$_2$)$_{2-5}$— or —(CH$_2$)O(CH$_2$)—;

R$^{14}$ is selected from the group: OH, H, C$_1$–C$_4$ alkyl, and benzyl;

R$^{16}$ is selected from the group: an amine protecting group, 1–2 amino acids and 1–2 amino acids substituted with an amine protecting group;

R$^{34}$ and R$^{35}$ are independently at each occurrence selected from the group: —OH, —F, —N(R$^{13}$)$_2$, and C$_1$–C$_8$-alkoxy;

R$^{34}$ and R$^{35}$ can alternatively be taken together form:
a cyclic boron ester where said chain or ring contains from 2 to 20 carbon atoms and, optionally, 1–4 heteroatoms independently selected from N, S, and O;
a divalent cyclic boron amide where said chain or ring contains from 2 to 20 carbon atoms and, optionally, 1–4 heteroatoms independently selected from N, S, and O; or
a cyclic boron amide-ester where said chain or ring contains from 2 to 20 carbon atoms and, optionally, 1–4 heteroatoms independently selected from N, S, and O;

Pg is a thiol protecting group;
m is 1 or 2;
n is 0, 1, or 2;
p' is 0, 1, or 2;
q is 1 or 2;
q' is 0, 1, or 2;
s is 0, 1, 2, or 3;
t is 2, 3, or 4;
u is 2, 3, 4, or 5; and,
v is 1 or 2.

2. A reagent according to claim 1, wherein the reagent is of formula (II):

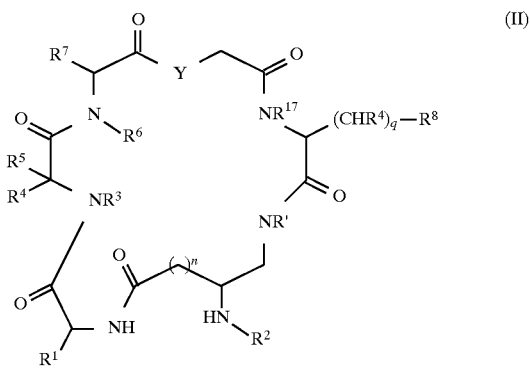

or a pharmaceutically acceptable salt or prodrug form thereof.

3. A reagent according to claim 2, wherein:
R', R$^3$, R$^4$, R$^6$, and R$^{17}$ are independently selected from the group: H, methyl, and ethyl;
Y is NH;
R$^5$ is selected from the group:
H, F, Cl, —CF$_3$, —CN, —C$_2$R$^{13}$, —C(=O)R$^{13}$, —C(=O)N(R$^{13}$)$_2$, —CH$_2$R$^{13}$, —N(R$^{13}$)$_2$,
C$_1$–C$_8$ alkyl substituted with 0–2 R$^{11}$;
C$_2$–C$_8$ alkenyl substituted with 0–2 R$^{11}$;
C$_3$–C$_{10}$ cycloalkyl substituted with 0–2 R$^{11}$;
aryl substituted with 0–2 R$^{12}$;
a 5–10-membered heterocyclic ring system containing 1–4 heteroatoms independently selected from N, S, or O, said heterocyclic ring being substituted with 0–2 R$^{12}$;
—C$_0$–C$_6$ alkyl-X;
—(CH$_2$)$_{q'}$-phenyl-(CH$_2$)$_{q'}$—X, wherein substitution on the phenyl is 1,4;
—CH$_2$-cyclohexyl-CH$_2$X, wherein substitution on the cyclohexyl is 1,4; and,
—(CH$_2$)$_m$S(O)$_{p'}$(CH$_2$)$_2$X;

R$^8$ is selected from the group: —CO$_2$R$^{13}$, —SO$_3$R$^{13}$, —SO$_2$NHR$^{14}$, —NHSO$_2$CF$_3$, —CONHNHSO$_2$CF$_3$, —PO(OR$^{13}$)$_2$, —PO(OR$^{13}$)R$^{13}$, —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$, and —SO$_2$NH-heteroaryl, said heteroaryl being 5–10-membered and having 1–4 heteroatoms selected independently from N, S, or O; and, R$^{12}$ is independently selected at each occurrence from the group: phenyl, benzyl, phenethyl, phenoxy, benzyloxy, halogen, hydroxy, nitro, cyano, C$_1$–C$_5$ alkyl, C$_3$–C$_6$ cycloalkyl, C$_3$–C$_6$ cycloalkylmethyl, C$_{6-10}$ aryl-C$_{1-6}$ alkyl, C$_1$–C$_5$ alkoxy, —CO$_2$R$^{13}$, —C(=O)NHOR$^{13a}$, —C(=O)NHN(R$^{13}$)$_2$, =NOR$^{13}$, C$_3$–C$_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —$SR^{13}$, —$SO_2N(R^{13})_2$, $C_2$–$C_6$ alkoxyalkyl, methylenedioxy, ethylenedioxy, $C_1$–$C_4$ haloalkyl, $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, and $C_{1-4}$ alkyl, said $C_{1-4}$ being substituted with 1–5 groups selected independently from the group: —$N(R^{13})_2$, —$CF_3$, $NO_2$, and —$S(=O)R^{13a}$.

4. A reagent according to claim 3, wherein:

$R^5$ is selected from the group:

H;

$C_1$–$C_8$ alkyl substituted with 0–2 $R^{11}$;

aryl substituted with 0–2 $R^{12}$; and, a 5–10-membered heterocyclic ring system containing 1–4 heteroatoms independently selected from N, S, or O, said heterocyclic ring being substituted with 0–2 $R^{12}$;

X is selected from the group: $NHC(=NR^{13})N(R^{13})R^{13}$, —$N(R^{13})R^{13}$, —$C(=NH)(NH_2)$, and —NH—C$(=N—OR^{13})(NH_2)$;

$R^8$ is selected from the group: —$CO_2R^{13}$, —$SO_3R^{13}$, and —$SO_2NHR^{14}$; and, $R^{12}$ is independently selected at each occurrence from the group: phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_{6-10}$ aryl-$C_{1-6}$ alkyl, $C_1$–$C_5$ alkoxy, —$CO_2R^{13}$, $C_3$–$C_6$ cycloalkoxy, —$OC(=O)R^{13}$, —$C(=O)R^{13}$, —$OC(=O)OR^{13a}$, —$OR^{13}$, —($C_1$–$C_4$ alkyl)-$OR^{13}$, —$N(R^{13})_2$, $C_2$–$C_6$ alkoxyalkyl, methylenedioxy, ethylenedioxy, $C_1$–$C_4$ haloalkyl, $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —$OCH_2CO_2H$, and $C_{1-4}$ alkyl, said $C_{1-4}$ alkyl being substituted with 1–5 groups selected independently from the group: —$N(R^{13})_2$, —$CF_3$, $NO_2$, and —$S(=O)R^{13a}$.

5. A reagent according to claim 4, wherein the reagent is of formula (III):

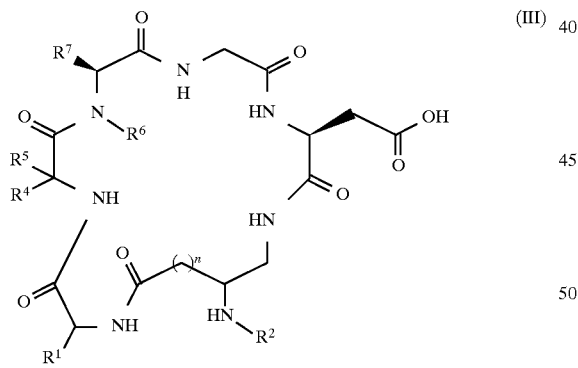

(III)

wherein, $R^1$ is $C_{1-4}$ alkyl substituted with 0–1 $R^{20a}$;

$R^{20a}$ is independently selected at each occurrence from the group: —CN, —$CO_2R^{21}$, —$C(=O)R^{21a}$, $C(=O)$ $CH_2R^{21}$, $C(=O)NR^{22}C(=O)R^{21a}$, $C(=O)$ $OCH_2CO_2H$, $C(=O)NR^{23}R^{24}$, —$C(=O)N(R^{22})_2$, —$CH_2R^{21}$, —$OC(=O)R^{21a}$, —$OC(=O)OR^{21a}$, —$OR^{21a}$, —$OC(=O)N(R^{22})_2$, —$NR^{22}C(=O)R^{21a}$, —$NR^{22}C(=O)OR^{21}$, —$NR^{22}C(=O)N(R^{22})_2$, —$N(R^{22})_2$, =$NOR^{21}$, —$C(=O)NHOR^{21}$, —$C(=O)$ $NHNR^{22}R^{22}$, —$OCH_2CO_2H$, $NR^{23}R^{24}$, —$NR^{22}SO_2N$ $(R^{22})_2$, —$NR^{22}SO_2R^{21b}$, —$SO_3H$, —$SO_2R^{21b}$, —$SR^{21}$, —$S(=O)R^{21b}$, —$SO_2N(R^{22})_2$, $SCH_2NR^{22}C$ $(=O)R^{21}$, SH, S(Pg), =O, OH, $PR^{25}R^{26}$, $P(O)R^{25}R^{26}$, $P(S)R^{25}R^{26}$, and $P(NR^{27})R^{25}R^{26}$;

$R^{23}$, $R^{24}$, $R^{25}$, $R^{26}$, and $R^{27}$ are each independently selected at each occurrence from the group:

hydrogen;

$C_{1-10}$ alkyl substituted with 0–3 $R^{40}$;

$C_{6-10}$ aryl substituted with 0–3 $R^{40}$;

$C_{3-8}$ cycloalkyl substituted with 0–3 $R^{40}$;

heterocyclyl-$C_{1-6}$ alkyl substituted with 0–3 $R^{40}$, wherein the heterocycle is selected from the group: pyridine, pyrazine, proline, furan, thiofuran, thiazole, and diazine; and an electron, provided that when one of $R^{23}$ or $R^{24}$ is an electron, then the other is also an electron, and provided that when one of $R^{25}$ or $R^{26}$ is an electron, then the other is also an electron;

$R^2$ is independently selected from the group: H, and $C_{1-4}$ alkyl substituted with 0–1 $R^{41}$;

$R^5$ is selected from the group:

H;

$C_{1-4}$ alkyl substituted with 0–2 $R^{11}$;

aryl substituted with 0–2 $R^{12}$; and, a 5–10-membered heterocyclic ring system containing 1–4 heteroatoms independently selected from N, S, or O, said heterocyclic ring being substituted with 0–2 $R^{12}$;

$R^7$ is selected from the group:

—$C_1$–$C_7$ alkyl-X; and,

—$(CH_2)_{q'}$-phenyl-$(CH_2)_{q'}$—X, wherein substitution on the phenyl is 1,3 or 1,4;

X is selected from the group: $NHC(=NR^{13})N(R^{13})R^{13}$, —$N(R^{13})R^{13}$, —$C(=NH)(NH_2)$, and —NH—C$(=N—OR^{13})(NH_2)$;

$R^{11}$ is independently selected at each occurrence from the group: =O, F, Cl, Br, I, —$CF_3$, —CN, —$CO_2R^{13}$, —$C(=O)R^{13}$, —$C(=O)N(R^{13})_2$, —CHO, —$CH_2OR^{13}$, —$OC(=O)R^{13}$, —$OR^{13}$, —$NR^{13}C(=O)$ $R^{13}$, —$NR^{14}SO_2R^{13a}$, —$N(R^{13})_2$, —$NHC(=NH)$ $NHR^{13}$, —$C(=NH)NHR_{13}$, $C_3$–$C_6$ cycloalkyl, $C_3$–$C_6$ cycloalkoxy, $C_{6-10}$ aryl substituted with 0–2 $R^{12}$, and a 5–10-membered heterocyclic ring system containing 1–4 heteroatoms independently selected from N, S, and O, said heterocyclic ring being substituted with 0–2 $R^{12}$;

$R^{12}$ is independently selected at each occurrence from the group: halogen, hydroxy, nitro, cyano, $C_1$–$C_5$ alkyl, $C_1$–$C_5$ alkoxy, —$CO_2R^{13}$, $C_3$–$C_6$ cycloalkoxy, —$C(=O)R^{13}$, —$OR^{13}$, —$N(R^{13})_2$, methylenedioxy, ethylenedioxy, $C_1$–$C_4$ haloalkyl, and $C_1$–$C_4$ haloalkoxy; and, $R^{13}$ is independently selected at each occurrence from the group: H, $C_1$–$C_{10}$ alkyl, $C_3$–$C_{10}$ cycloalkyl, $C_{1-4}$ alkyl-$C_{3-6}$ cycloalkyl, $C_{6-10}$ aryl, —$C_{1-10}$ alkyl-$C_{6-10}$ aryl, and $C_{1-6}$ alkoxy-$C_{1-6}$ alkyl.

6. A reagent according to claim 5, wherein $R^1$ is $CH_2S(Pg)$ and $R^2$ is selected from H, $CH_2CH_2S(Pg)$, $C(O)CH_2S(Pg)$, $CH_2C(CH_3)_2S(Pg)$, $C(O)C(CH_3)_2S(Pg)$, $CH_2(1$-hydroxyphen-2-yl), and $C(O)CH_2NH_2$.

7. A reagent according to claim 6, wherein the reagent is selected from the group:

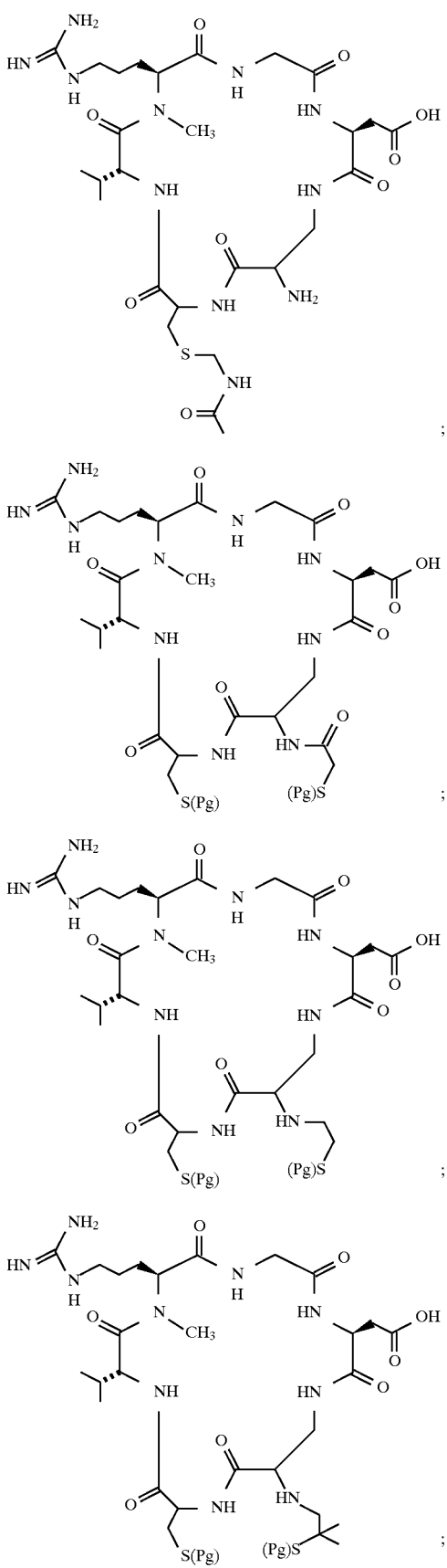

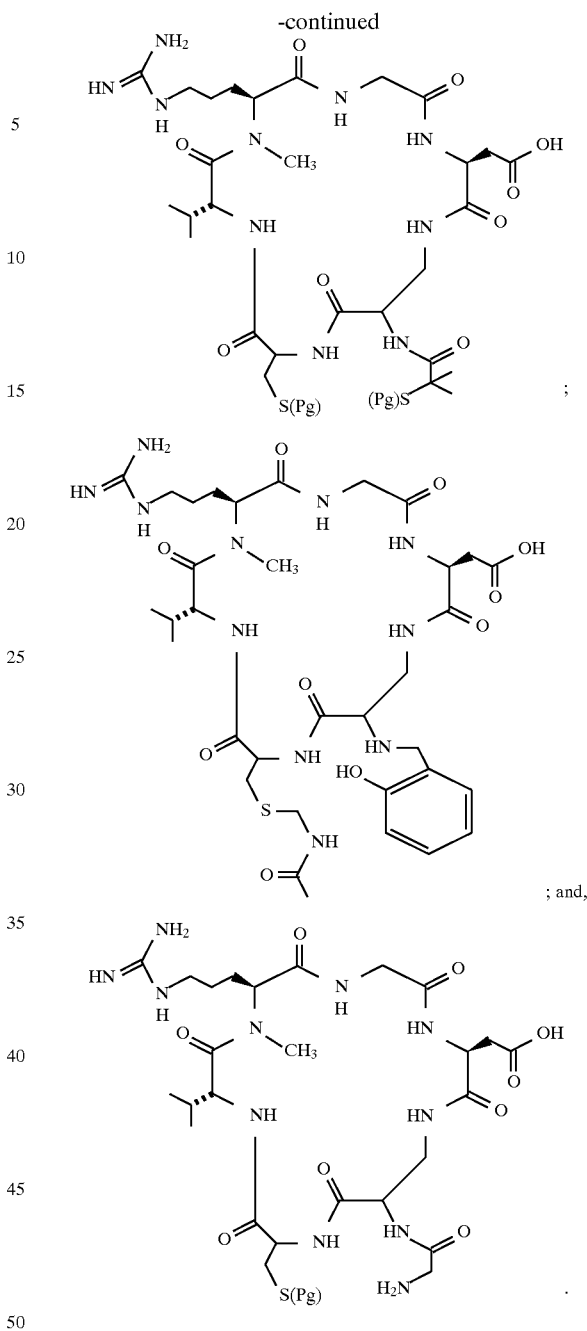

8. A reagent according to claim 7, wherein Pg is selected from acetamidomethyl, 1-ethoxyethyl, p-anisylidene, tetrahydropyranyl, and tetrahydrofuranyl.

9. A kit for preparing a radiopharmaceutical comprising a predetermined quantity of a sterile, pharmaceutically acceptable reagent of claim 1.

10. A radiopharmaceutical comprising a complex of a reagent of claim 1 and a radionuclide selected from the group $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, and $^{97}$Ru.

11. A radiopharmaceutical comprising a complex of a reagent of claim 1 and a radionuclide selected from the group $^{99m}$Tc, $^{111}$In, and $^{62}$Cu.

12. A radiopharmaceutial according to claim 11, wherein the radiopharmaceutical is a formula selected from the group:

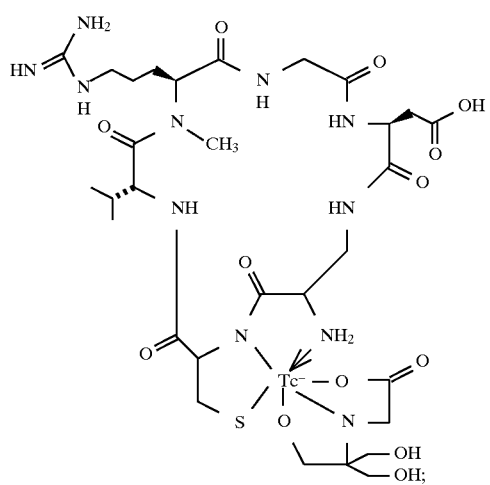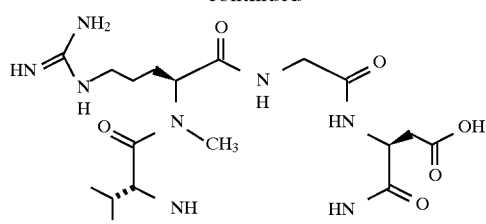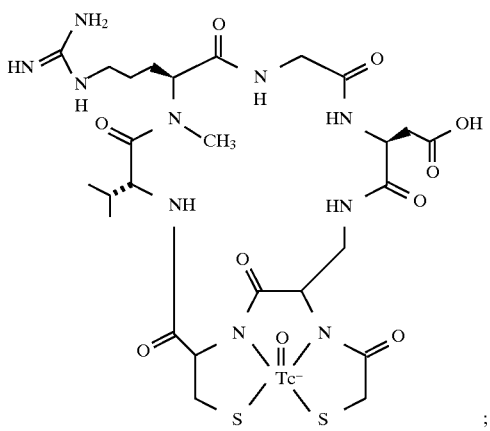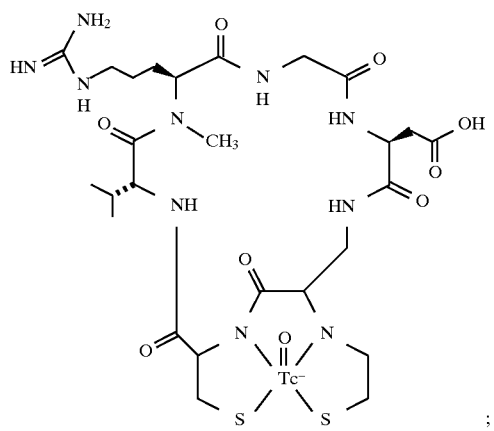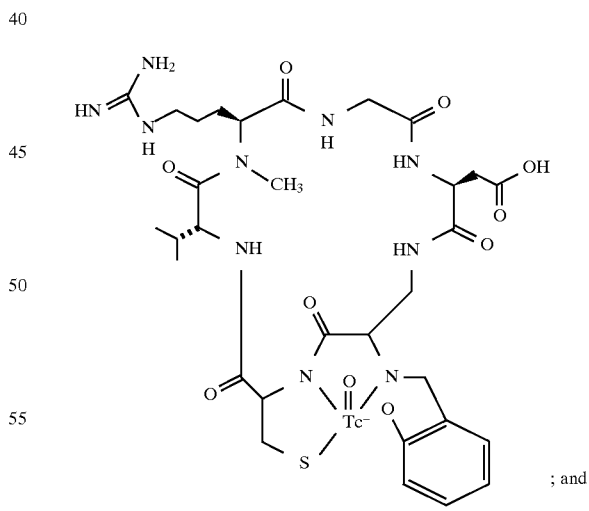

-continued

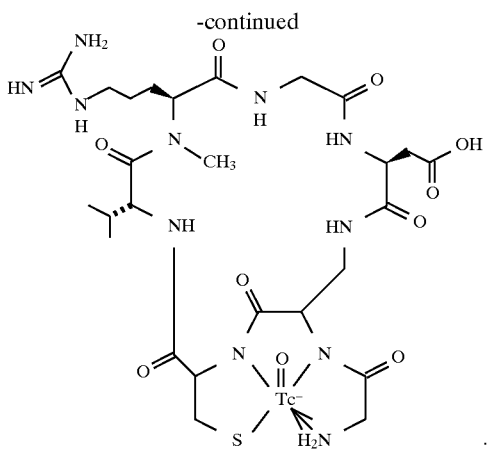

13. A radiopharmaceutical composition comprising a radiopharmaceutically acceptable carrier and a compound of claim 10, wherein the compound is radiolabeled.

14. A method for visualizing sites of platelet deposition in a mammal by radioimaging, comprising:
   (i) administering to said mammal an effective amount of a radiopharmaceutical of claim 10, and
   (ii) scanning the mammal using a radioimaging device.

15. A method of determining platelet deposition in a mammal, comprising:
   (a) administering to said mammal a radiopharmaceutical composition comprising a compound of claim 10, and
   (b) imaging said mammal.

16. A method of diagnosing a disorder platelet deposition in a mammal, comprising:
   (a) administering to said mammal a radiopharmaceutical composition comprising a compound of claim 10, and
   (b) imaging said mammal.

17. A kit for visualizing sites of platelet deposition, determining platelet deposition, or diagnosing a disorder platelet deposition in a mammal, comprising:
   (a) a predetermined quantity of a reagent of claim 1; and,
   (b) a predetermined quantity of a reducing agent.

18. A kit according to claim 17, wherein components (a) and (b) are contained in a vial.

19. A kit according to claim 17, wherein component (a) is contained in a first vial and component (b) is contained in a second vial.

* * * * *